(12) United States Patent
Rodan et al.

(10) Patent No.: US 11,471,364 B2
(45) Date of Patent: Oct. 18, 2022

(54) SKIN CLEANSING DEVICE HAVING INTERCHANGEABLE CLEANSING HEADS

(71) Applicant: Rodan & Fields, LLC, San Francisco, CA (US)

(72) Inventors: Kathryn Pregerson Rodan, Oakland, CA (US); Kathy A. Fields, San Francisco, CA (US); Steven D. Powell, Provo, UT (US)

(73) Assignee: RODAN & FIELDS, LLC, San Francisco, CA (US)

( * ) Notice: Subject to any disclaimer, the term of this patent is extended or adjusted under 35 U.S.C. 154(b) by 395 days.

(21) Appl. No.: 16/744,839

(22) Filed: Jan. 16, 2020

(65) Prior Publication Data
US 2020/0222269 A1 Jul. 16, 2020

Related U.S. Application Data

(60) Provisional application No. 62/902,649, filed on Sep. 19, 2019, provisional application No. 62/793,182, filed on Jan. 16, 2019.

(51) Int. Cl.
*A47K 7/00* (2006.01)
*A61H 7/00* (2006.01)
(Continued)

(52) U.S. Cl.
CPC .............. *A61H 7/005* (2013.01); *A61K 8/345* (2013.01); *A61K 8/368* (2013.01); *A61K 8/37* (2013.01);
(Continued)

(58) Field of Classification Search
CPC ... A47K 7/00; A47K 7/04; A47K 7/03; A47K 7/08; A47K 7/043; A47K 2010/326;
(Continued)

(56) References Cited

U.S. PATENT DOCUMENTS 5,187,827 A * 2/1993 Wei ........................ A47K 7/046
601/161
6,019,749 A 2/2000 Fields et al.
(Continued)

FOREIGN PATENT DOCUMENTS

JP 3864652 B2 1/2007

OTHER PUBLICATIONS

Notification, International Search Report and Written Opinion for PCT/US2020/013862 dated May 15, 2020.

*Primary Examiner* — Eisa B Elhilo
(74) *Attorney, Agent, or Firm* — Troutman Pepper Hamilton Sanders LLP

(57) ABSTRACT

A skin cleansing device has a base body and a removable cleansing head. The base body houses a vacuum pump and has a mount for connecting to the removable cleansing head. The mount has an opening into the base body and a support surface. The removable cleansing head has a collection portion and a mounting portion. The collection portion defines an inlet and an internal cavity. The mounting portion has a stem defining a channel fluidly connected to the internal cavity. The cleansing head is removably connectable to the base body with the stem being configured to be received in the opening of the mount. The vacuum pump is configured to generate a fluid flow through the internal cavity and the channel into the base body such that a suction force is generated at the inlet.

20 Claims, 12 Drawing Sheets

(51) Int. Cl.
*A61M 1/00* (2006.01)
*A61K 8/73* (2006.01)
*A61K 8/81* (2006.01)
*A61K 8/368* (2006.01)
*A61K 8/37* (2006.01)
*A61K 8/9789* (2017.01)
*A61K 8/34* (2006.01)

(52) U.S. Cl.
CPC ............... *A61K 8/73* (2013.01); *A61K 8/8152* (2013.01); *A61K 8/9789* (2017.08); *A61M 1/0003* (2013.01); *A61H 2201/0107* (2013.01); *A61H 2201/0153* (2013.01); *A61H 2201/0157* (2013.01); *A61K 2800/87* (2013.01)

(58) Field of Classification Search
CPC .. A47K 5/14; A61H 7/005; A61H 2201/0107; A61M 1/0003; A61M 8/8152; A61K 8/9789; A61K 8/368; A61K 8/8152
USPC ........................................................ 606/131
See application file for complete search history.

(56) References Cited

U.S. PATENT DOCUMENTS

| | | |
|---|---|---|
| 6,241,739 B1 | 6/2001 | Waldron |
| 7,320,691 B2 | 1/2008 | Pilcher et al. |
| 7,396,352 B2 | 7/2008 | Ikadai |
| 7,431,718 B2 | 10/2008 | Ikadai |
| D723,160 S | 2/2015 | Rodan et al. |
| 8,961,450 B2 | 2/2015 | Anderson et al. |
| 2001/0041848 A1 | 11/2001 | Ito et al. |
| 2003/0114804 A1 | 6/2003 | Putzer |
| 2006/0058714 A1* | 3/2006 | Rhoades ............... A46B 5/0016 601/72 |
| 2007/0256262 A1* | 11/2007 | Moss ................. A61C 17/3418 15/176.1 |
| 2009/0124985 A1* | 5/2009 | Hasenoehrl ............ A61Q 19/00 604/289 |
| 2015/0051620 A1 | 2/2015 | Presser et al. |

\* cited by examiner

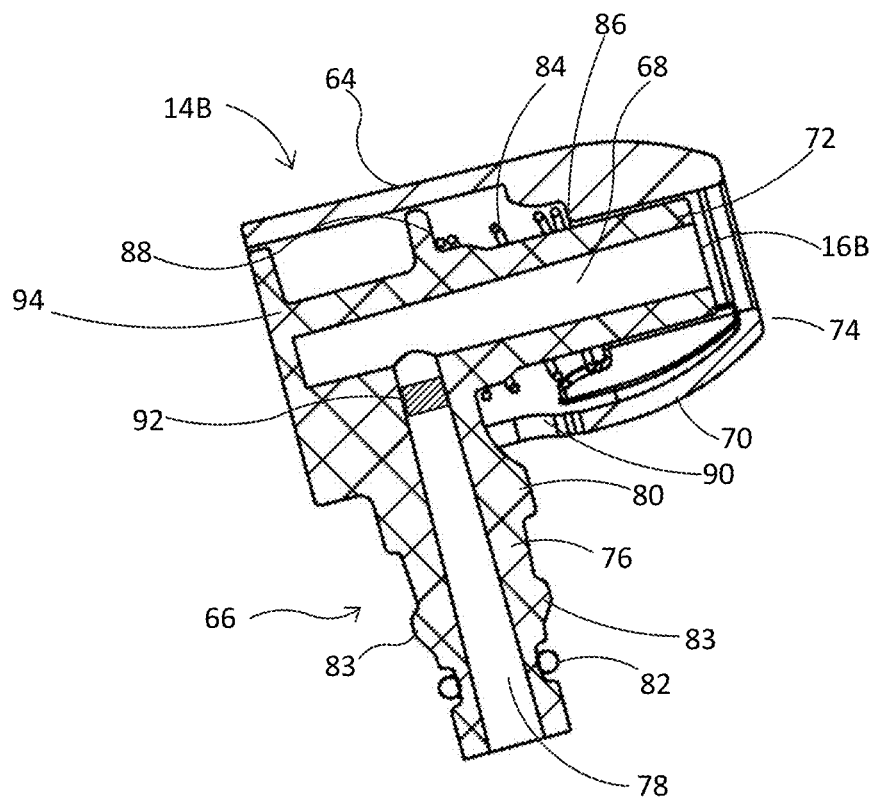
FIG. 7
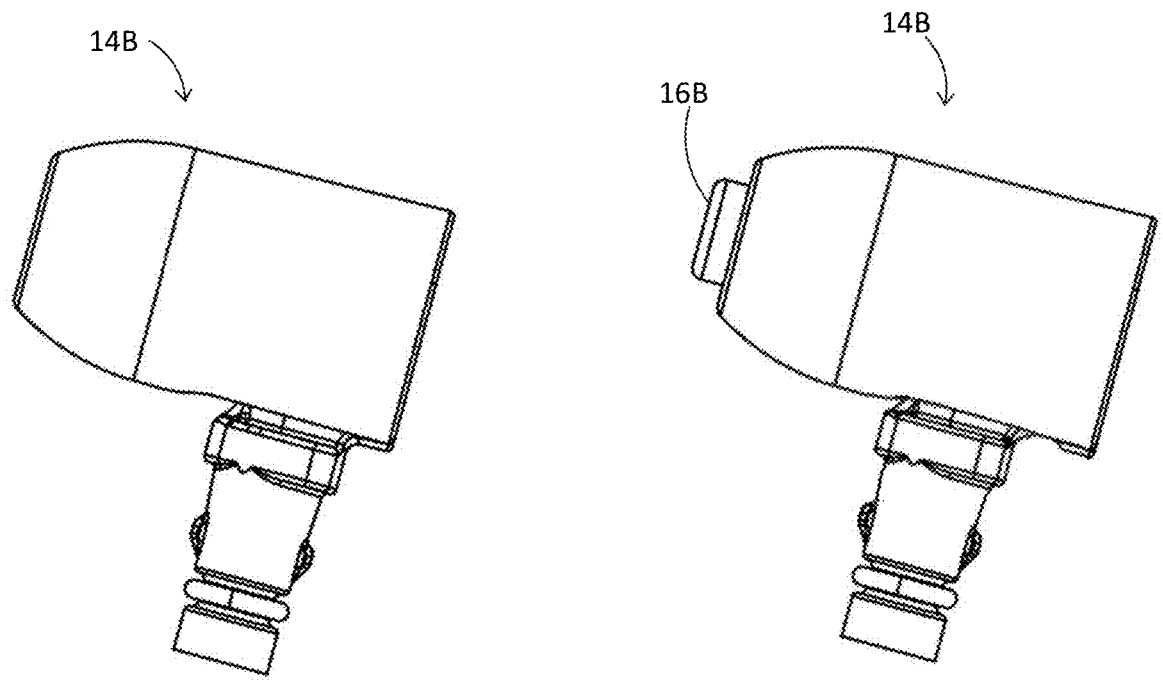
FIG. 8A  FIG. 8B

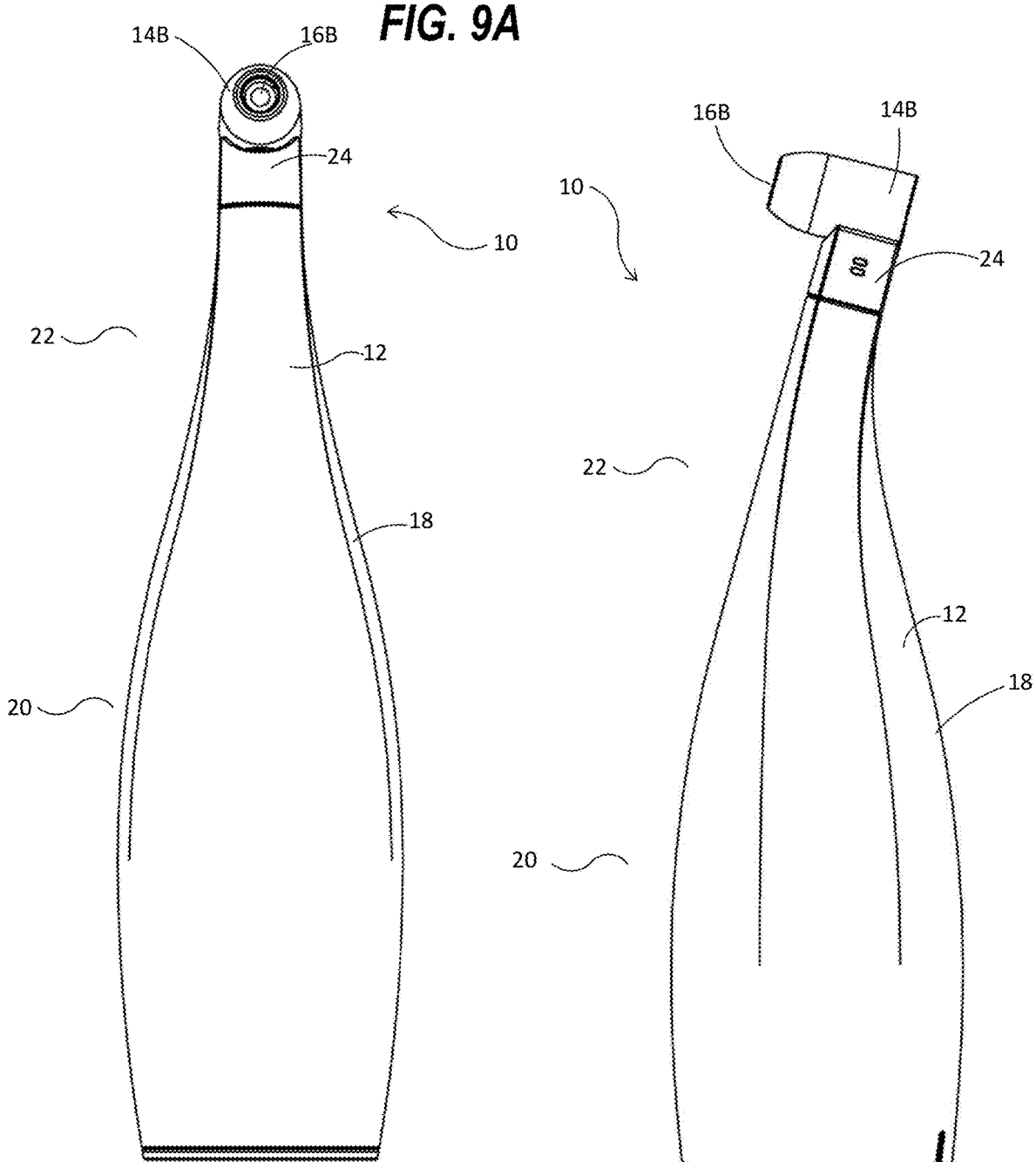

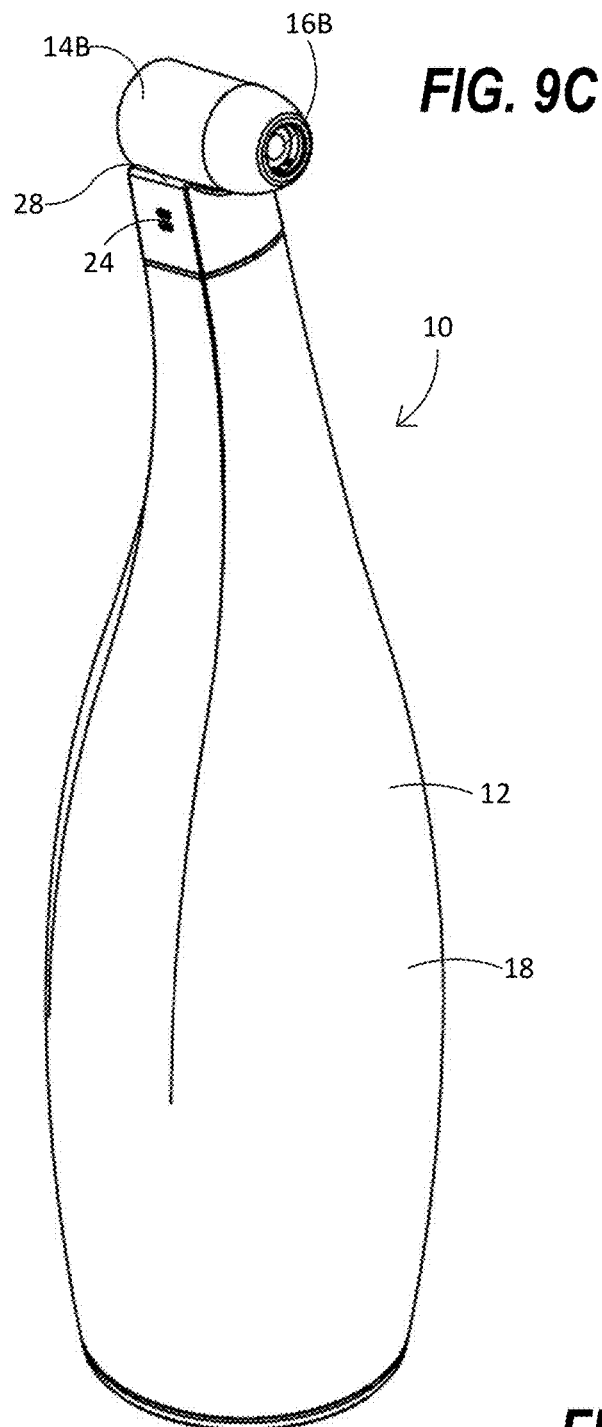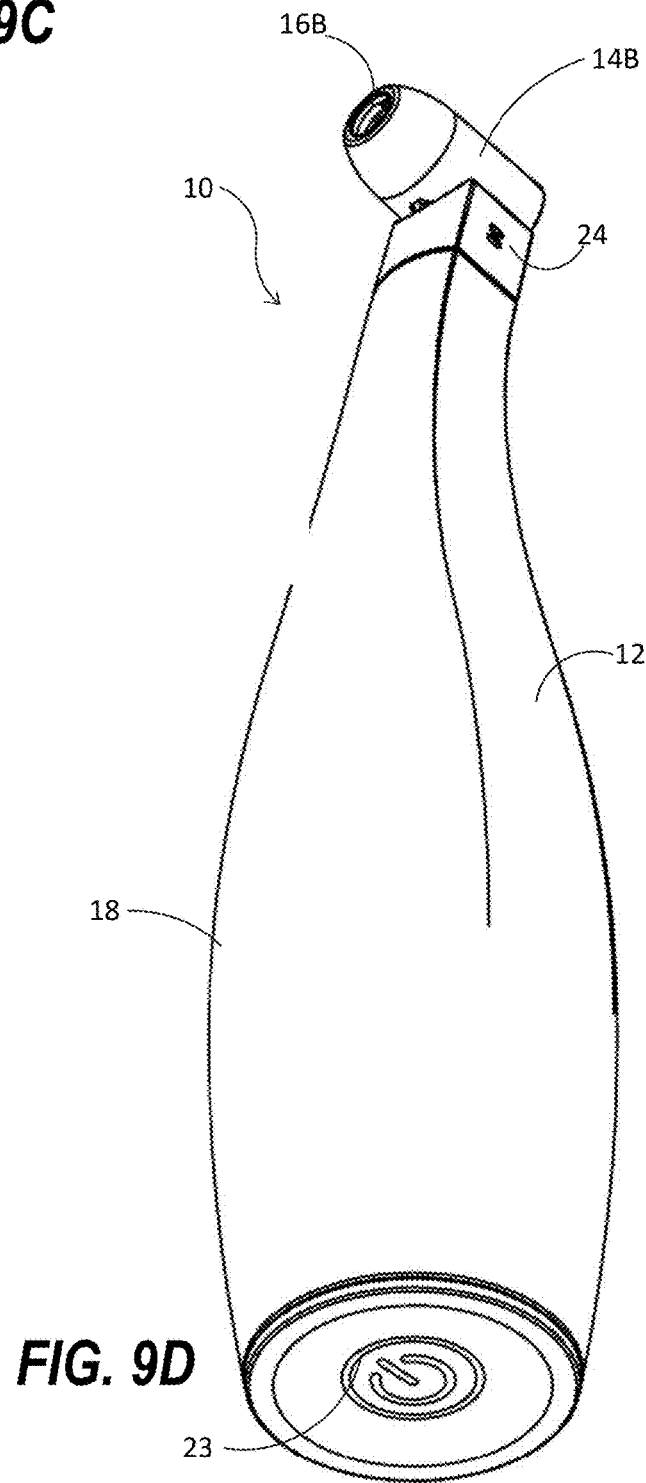
FIG. 9C
FIG. 9D

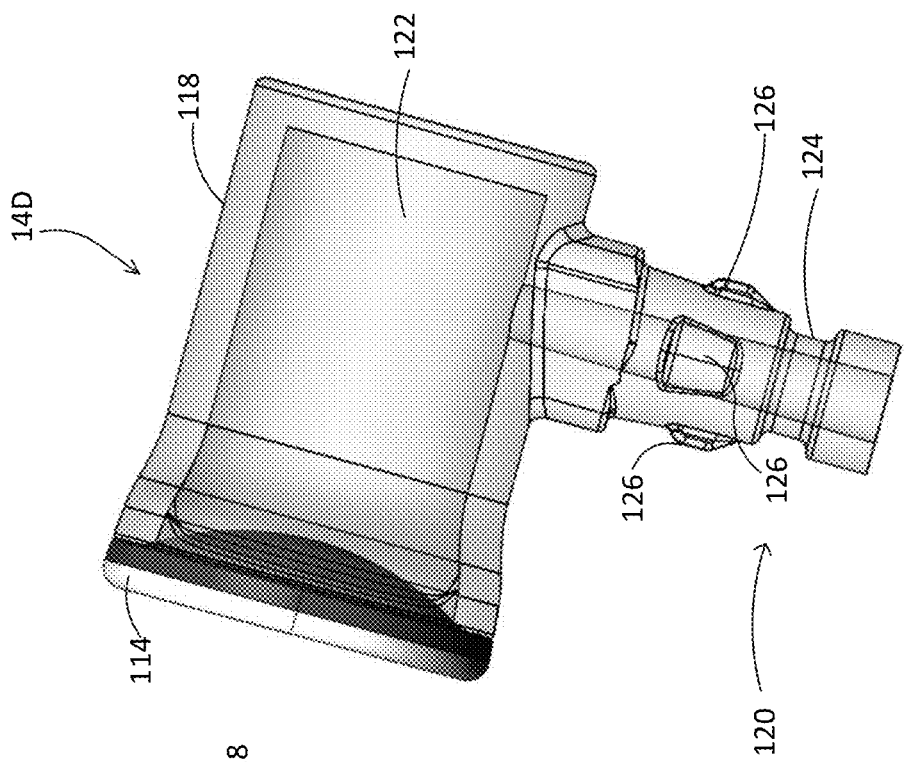
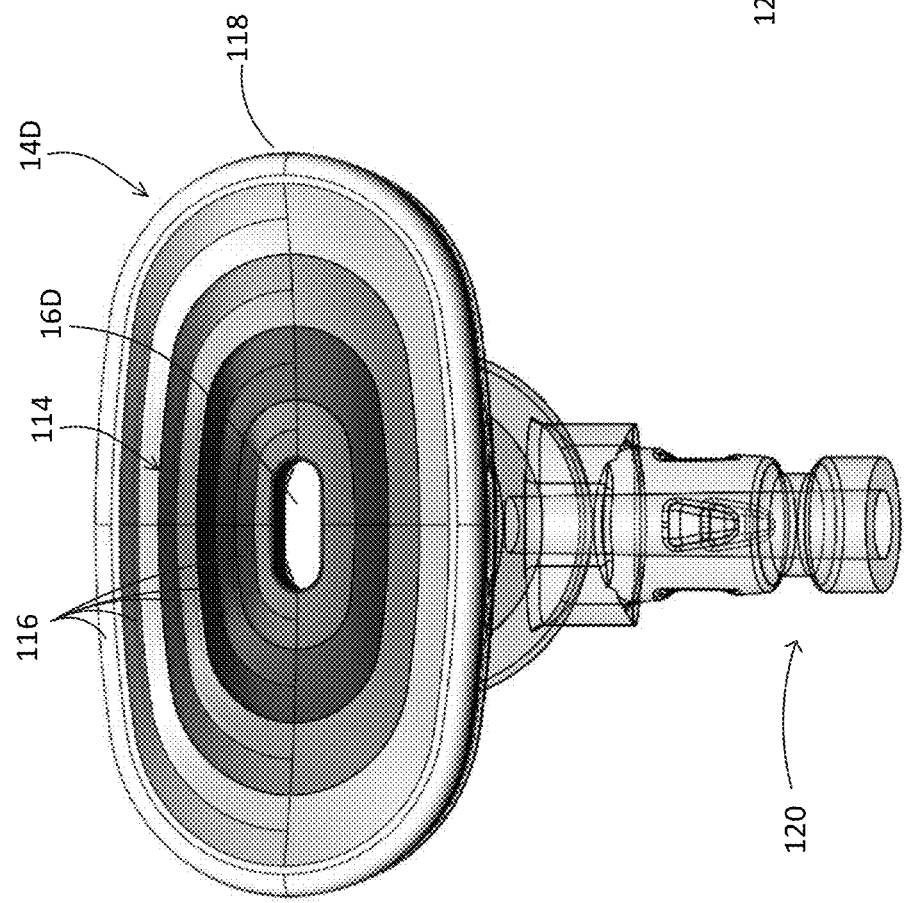
FIG. 11B
FIG. 11A

SKIN CLEANSING DEVICE HAVING INTERCHANGEABLE CLEANSING HEADS

PRIORITY CLAIM

This application claims the benefit of priority of U.S. Provisional Patent Application No. 62/793,182, filed on Jan. 16, 2019 and U.S. Provisional Patent Application No. 62/902,649, filed on Sep. 19, 2019, the entire contents of both of which are hereby incorporated by reference herein.

TECHNICAL FIELD

The present disclosure generally relates to a skin cleansing device, and more particularly to a hand-held device with an interchangeable head for selectively targeting skin areas for cleansing.

BACKGROUND

Proper skin care is important for heath and cosmetic reasons. Skin is a vital organ and a breakdown in the skin can adversely affect the skin's function as a barrier and make it susceptible to infection. A breakdown in the skin can also be very painful, such as the case of excessive dry skin. Visual irregularities in the skin can adversely affect a person's confidence and other people's perceptions.

Various cleansing devices and products have been developed that target removal of unwanted materials from the skin, such as through pore cleansing. Some devices utilize vacuum suction to draw material out of pores. However, such devices are often only available in a medical professional setting and may be uncomfortable and unsuitable for personal use. Further, the devices that have been developed for personal at-home use do not provide versatility that may be needed to address different skin areas and/or to provide a variety of skin cleansing options.

The present disclosure is directed to providing an improved skin cleansing device that overcomes at least some of the problems of current skin cleansing devices.

SUMMARY

In some embodiments, the present disclosure is directed to a skin cleansing device. The skin cleansing device includes a base body and a removable cleansing head. The base body houses a vacuum pump and includes a mount, the mount including an opening into the base body and a support surface. The removable cleansing head includes a collection portion and a mounting portion, the collection portion defining an inlet and an internal cavity and the mounting portion comprising a stem defining a channel fluidly connected to the internal cavity. The cleansing head is removably connectable to the base body with the stem being configured to be received in the opening of the mount. The vacuum pump is configured to generate a fluid flow through the internal cavity and the channel into the base body such that a suction force is generated at the inlet.

In another embodiment, the present disclosure is directed to a cleansing head for use with a base body configured to produce a fluid flow into an opening via a vacuum pump. The cleansing head includes a collection portion including an outer housing defining an aperture and an inner nozzle defining an internal cavity and an inlet. The outer housing is movable relative to the inner nozzle between a first position in which the inlet is retracted inside the outer housing and a second position in which the inlet is outside of or at least flush with the aperture. The cleansing head also includes a mounting portion including a stem extending away from the collection portion. The stem defines a channel fluidly connected to the internal cavity to create a flow path from the inlet to an outlet of the channel.

In still other embodiments, the present disclosure is directed to a skin care kit. The skin care kit may include a skin care composition configured to prepare the skin for use with a skin cleansing device disclosed herein. The skin care kit may further include the skin cleansing device, including the base body and at least one removable cleansing head configured to be connected to the base body.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures:

FIG. 7 is a cross-sectional view of the second cleansing head, taken along line C-C of FIG. 6C;

FIG. 8A is a side view of the second cleansing head with relatively-movable components in a first position;

FIG. 8B is a side view of the second cleansing head in a second position;

FIG. 9A is a front view of the exemplary skin cleansing device of FIG. 1, including the second cleansing head;

FIG. 9B is a side view of the exemplary skin cleansing device with the second cleansing head;

FIG. 9C is a top perspective view of the exemplary skin cleansing device with the second cleansing head;

FIG. 9D is a bottom perspective view of the exemplary skin cleansing device with the second cleansing head;

FIG. 11A is a front view of an example embodiment of a fourth cleansing head; and FIG. 11B is a side view of the exemplary fourth cleansing head of FIG. 11A.

DETAILED DESCRIPTION

Figure 1:
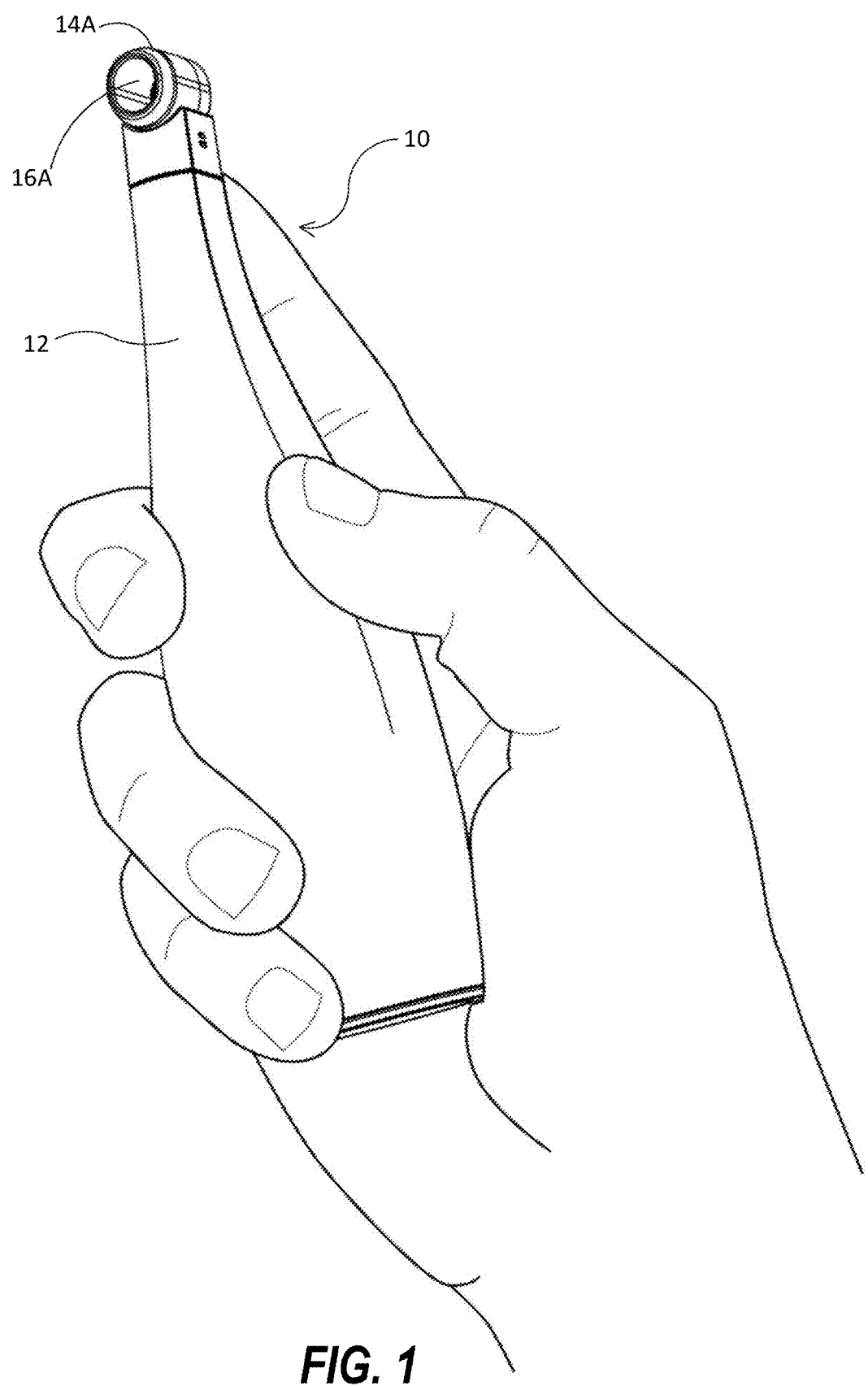
FIG. 1 is a perspective view of an example embodiment of a skin cleansing device being held by a user.

The present disclosure describes embodiments of a skin cleansing device. The skin cleansing device includes a base body sized for hand-held use and one or more cleansing heads which are removably connectable to the base body. The base body houses internal components which are configured to generate suction that is translated through the attached cleansing head. For example, the base body may include a vacuum pump that creates suction in a vacuum line fluidly connected to the cleansing head. The vacuum pump thereby generates a suction force at an inlet of the cleansing head. A user may apply the cleansing head to a targeted skin area in order to utilize the suction force to draw material out and/or off of the skin, such as to cleanse and unclog pores, remove blackheads, and the like.

In at least some embodiments, the base body is configured for interchangeable connection with a plurality of different cleansing heads to provide a degree of versatility to the device. For example, a first cleansing head may include a broader, larger inlet that allows for general skin cleansing of a relatively large area fairly quickly. A second cleansing head may include a smaller inlet that may be used to target specific spots or areas of skin, such as the location of a blackhead or clogged pore. Other cleansing heads may be provided and may include alternative and/or additional features configured to perform cleansing tasks during use. The combined base body and plurality of interchangeable heads may be provided as part of a cleansing kit.

In some embodiments, at least one interchangeable cleansing head may include relatively-movable components that enhance the functionality of the device, such as to improve comfort and use of the device. For example, a cleansing head may be configured with an outer housing that is slidable with respect to an inner nozzle such that the inner nozzle is retracted into the outer housing prior to use. The outer housing may be formed as a tubular shell and the inner nozzle formed as an inlet nozzle for containing the fluid flow produced by the vacuum pump. The inlet nozzle may be directed to a specific spot on the user's skin by the outer housing being placed at the spot and applying a force to slide the outer housing, moving the inlet nozzle inward until it contacts the skin.

In some embodiments, a cleansing composition may be provided and used in combination with the cleansing device to enhance the cleansing functionality. The cleansing composition may be selected from a group of skin care agents that prepare the skin for a cleansing process using a disclosed cleansing device. For example, the composition may prepare pores for a blackhead removal process using a blackhead removal head as part of the cleansing device. The preparation may include softening the skin, enlarging the pores, or otherwise treating the skin prior to applying the suction force provided by the skin cleansing device. One or more cleansing compositions in the form of a skin care agent may be provided with the skin cleansing device as part of a kit.

FIG. 1 is a perspective view of an exemplary embodiment of a skin cleansing device 10 being held by a user. The skin cleansing device 10 includes a base body 12 and a cleansing head 14A. The base body 12 is preferably configured to be held in a user's hand and may include an elongated shape leading up to the cleansing head 14A. The cleansing head 14A is preferably removably connectable to the upper portion of the base body 12 such that a plurality of cleansing heads may be interchangeably selected and connected to the base body 12. The user may move the skin cleansing device 10 such that the cleansing head 14A is against or adjacent to a targeted area of skin and the base body 12 (via internal components) may produce a suction force at an inlet 16A of the cleansing head 14A, to thereby draw materials out and off of the skin. For example, the suction force may draw a portion of skin itself into the inlet 16A with the materials (e.g., dirt, debris, blackheads, cleansers, makeup, cosmetics, etc.) being drawn into a cavity of the cleansing head 14A. Each cleansing head 14A may be a self-enclosed element that may be selectively connected to the base body to transfer, concentrate, and/or target a suction force generated by the skin cleansing device 10.

FIGS. 2A-2D further illustrate an exemplary embodiment of the base body 12. The base body 12 may include an outer surface 18 for being gripped and held by a user. The base body 12 may include an ergonomic shape that promotes ease of use with regard to placing a connected cleansing 14A head at a desired location on the skin. For example, the base body 12 may include an enlarged lower portion 20 that creates a larger base for holding by the user and a narrowed upper portion 22 that extends from the lower portion 20 and connects to the cleansing head 14A. The lower portion 20 may include a curved or rounded shape while the upper portion 22 is formed as a square or rectangular neck, although embodiments are not limited to this configuration. A primary axis P1 upper portion 22 may extend at an angle or slope backward slightly such that the cleansing head 14A presents at an angle with respect to a primary axis P2 of the lower portion 20 of the base body 12. This configuration may allow for more comfortable gripping of the base body 12 and placement of the cleansing head 14A during use of the skin cleansing device 10. Moreover, the cleansing head 14A may be configured such that a primary axis P3 the cleansing head 14A is perpendicular to the primary axis P1 of the neck of the upper portion 22. For example, the primary axis P3 around which the inlet 16A is formed may extend at an approximate 90 degree angle with respect to the primary axis P1 of the neck of the upper portion 22 of the base body 12. This configuration may provide an effective viewing angle for the user to view placement of the cleansing head 14A on their own skin. However, it should be understood that embodiments are not limited to the relative positioning of the components as illustrated.

The base body 12 may include the outer surface 18 being formed as part of an outer shell that encloses internal components that generate the suction force for the skin cleansing device 10. The internal components may, in some embodiments, be controlled by at least one control button 23 that is accessible on or around the outer shell of the base body 12. In some embodiments, the control button 23 may be positioned at a downward-facing bottom surface of the base body 12. The outer shell of the base body 12 may include other features, such as an exhaust opening/vent. The base body 12 may be formed as a single component or may be made up of more than one connected components.

The base body 12 may further include a mount 24 for the connecting to a selected cleansing head 14A. The mount 24 may be positioned at a top of the upper portion 22. The mount 24 may include an opening 26 (shown in FIG. 3) that leads into an interior of the base body 12. The mount 24 may further include a support surface 28 for supporting and contacting a portion of the cleansing head 14A. The support surface 28 may be shaped and configured to mate with a corresponding shape of the cleansing head 14A. In an exemplary embodiment, the support surface 28 includes a rounded, concave shape to receive a corresponding rounded shape of the cleansing head 14A. The mount 24 may include one or more sealing elements, such as a gasket, O-ring, or the like to create a seal when connected to the cleansing head 14A. The mount 24 allows the base body 12 to be connected to one of a variety of cleansing heads that may be at least partially inserted into the opening 26 in order to create a fluidic connection to allows a suction force originating in the base body 12 to be translated to the inlet 16A of the cleansing head 14A.

Figure 2A:
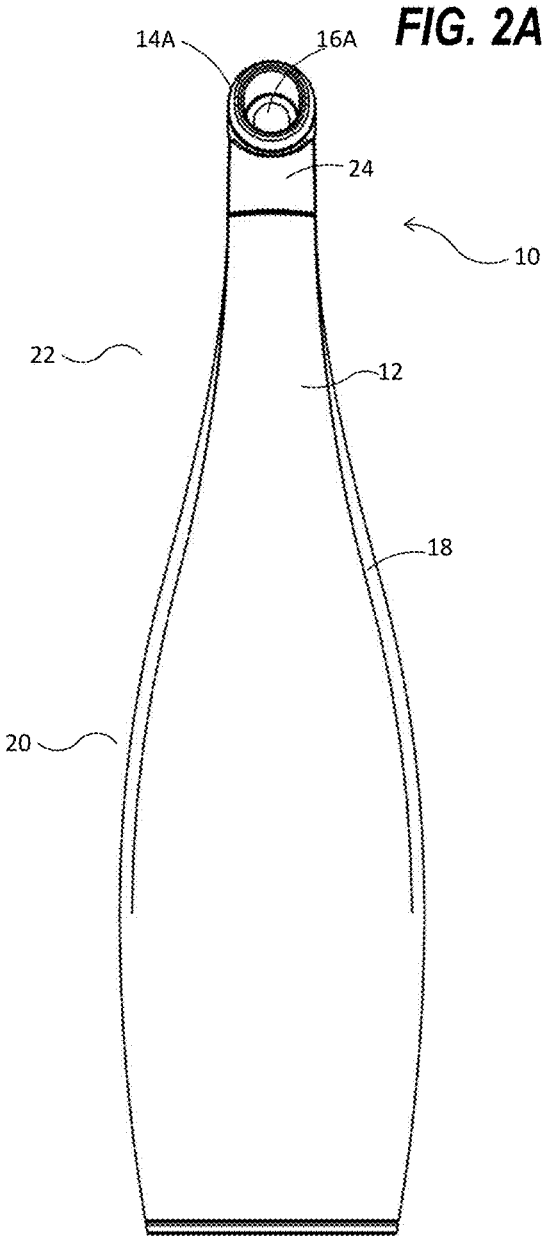
FIG. 2A is a front view of the exemplary skin cleansing device of FIG. 1.
Figure 2B:
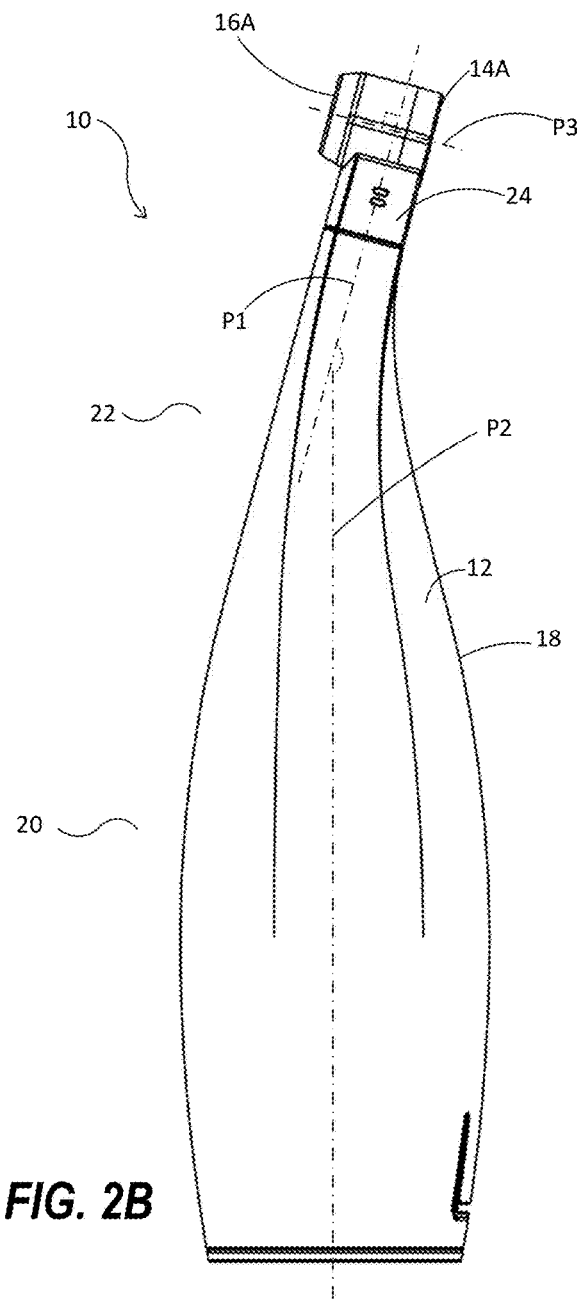
FIG. 2B is a side view of the exemplary skin cleansing device.
Figure 2C:
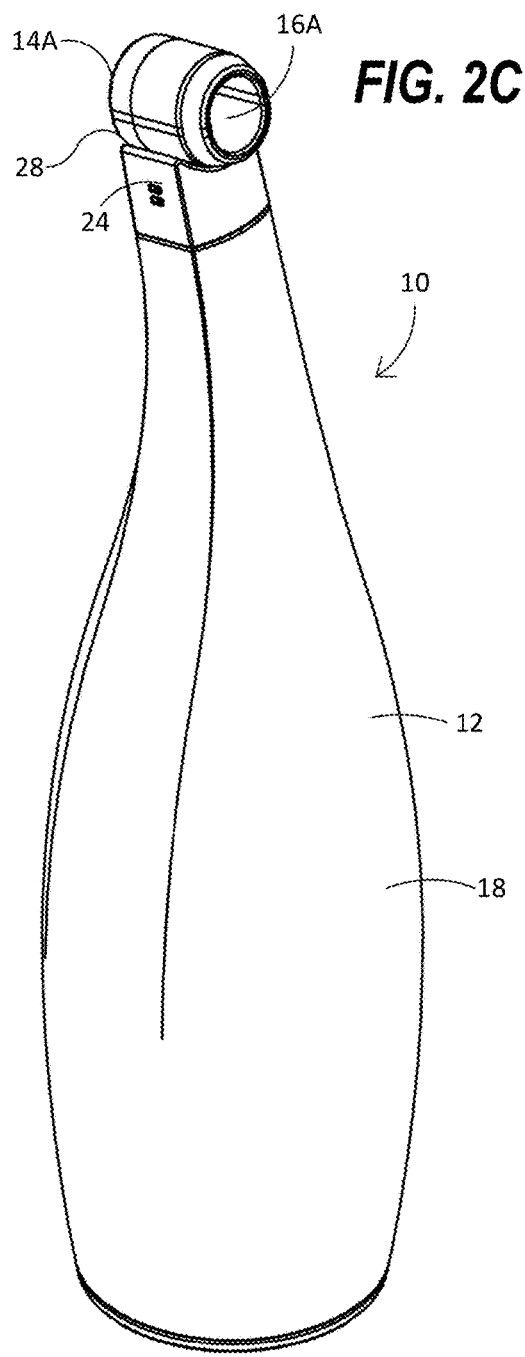
FIG. 2C is a top perspective view of the exemplary skin cleansing device.
Figure 2D:
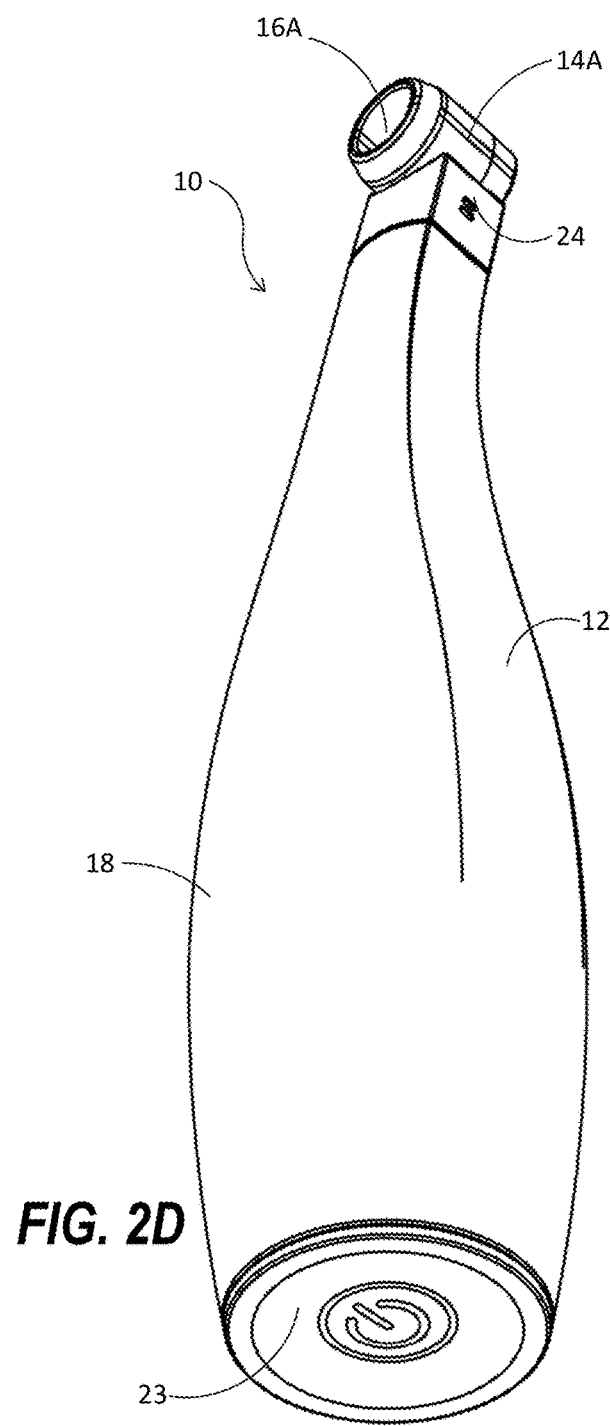
FIG. 2D is a bottom perspective view of the exemplary skin cleansing device.
Figures 3, 5B:
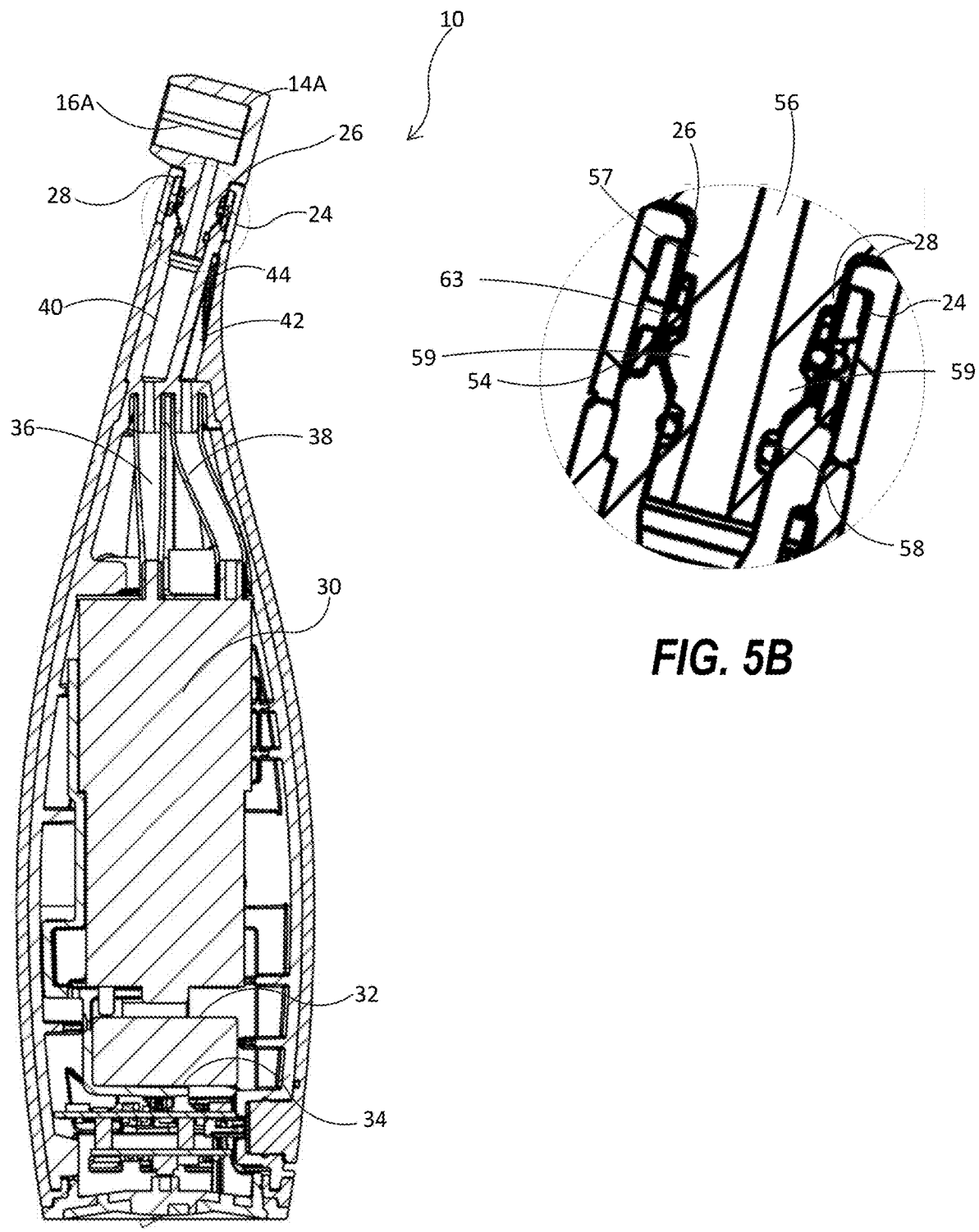
FIG. 3 is a cross-sectional view of the exemplary skin cleansing device, taken along line A-A of FIG. 2A.
FIG. 5B is a close-up cross-sectional view of an exemplary connection between a base body of the skin cleansing device and a cleansing head taken at the dotted circle of FIG. 3.

FIG. 3 is a cross-sectional view of the base body 12, taken along line A-A of FIG. 2A. The base body 12 preferably includes one or more internal cavities for housing internal components. The internal components include, for example, a vacuum pump 30, a power source (e.g., a battery) 32, a printed circuit board 34, a vacuum line 36, and an exhaust line 38. The base body 12 may also include one or more connecting channels that support fluid flow, such as a channel 40 to connect the vacuum line 36 to the opening 26 and a channel 42 to connect the exhaust line 38 to a vent 44. The term "channel" as used herein refers generally to a passageway configured to direct a flow of fluid (e.g., air) from place to another (e.g., one end of the channel to an opposite end of the channel) and it is not limited to being formed in any particular manner.

The vacuum pump 30 may be any of a number of devices configured to generate a suction force by pulling air into the vacuum pump 30 through the vacuum line 36 and expelling the air through the exhaust line 38. The vacuum pump 30 is preferably powered by the battery 32, which is also housed in the base body 12. The battery 32 may be, for example, a rechargeable battery. In another embodiment (not shown) a power cord could be used to power the device. The printed circuit board 34 may be a control element configured to send signals to and from the vacuum pump 30, such as to turn the vacuum pump 30 on and/or off. For example, the printed circuit board 34 may include electronic control elements that react to a pressing of the control button 23 by generating and sending an on/off signal to the vacuum pump 30 to selectively control operation of the vacuum pump 30. In operation, when the vacuum pump 30 is on, fluid flow is drawn down from the opening 26, through the channel 40, through the vacuum line 36, into the vacuum pump 30, and a corresponding fluid flow is created out of the vacuum pump 30, through the exhaust line 38, through the channel 42, and out of the vent 44.

FIGS. 4A-4E further illustrate an exemplary embodiment of the cleansing head 14A, which may be considered a first cleansing head 14A. The first cleansing head 14A may be a cleansing head configured for generic skin cleaning by creating a suction force at a broad inlet 16A. The first cleansing head 14A may be dragged across the user's skin to collect unwanted material (e.g., dirt, debris, cleanser, makeup, cosmetics, etc.) that may present. In an exemplary embodiment, the first cleansing head 14A may include a collection portion 46 and a mounting portion 48.

The collection portion 46 may be formed as a container for transferring fluid flow into the mounting portion 48 and receiving skin and/or material from the skin targeted by the first cleansing head 14A. For example, the collection portion 46 may include an internal cavity 50. The collection portion 46 may form the inlet 16A which is configured for contacting the skin. The collection portion 46 may include a contact surface 52 that surrounds the inlet 16A. The contact surface 52 may be angled or curved in a manner that gradually approaches the inlet 16A. In some embodiments, the inlet 16A may be optionally surrounded by a ring of soft contact material (e.g., rubber, silicone, etc.). The collection portion 46 may be formed a rounded head an include a shape that compliments the concave shape of the support surface 28. For example, the collection portion 46 may have a convex shape at a lower portion 20 thereof.

Figure 4A:
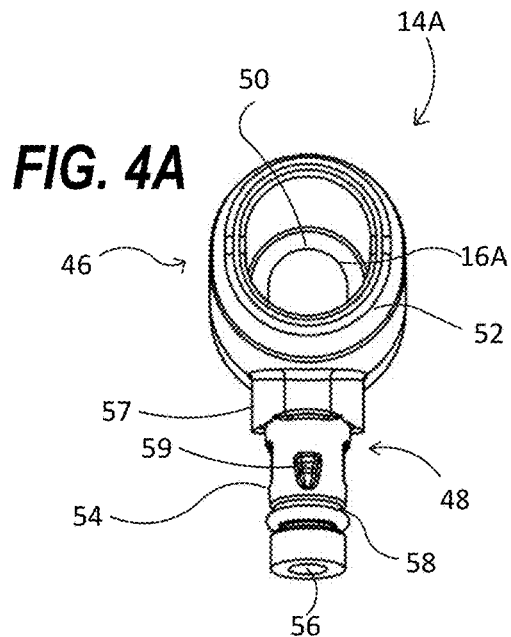
FIG. 4A is a front view of an example embodiment of a first cleansing head.
Figure 4B:
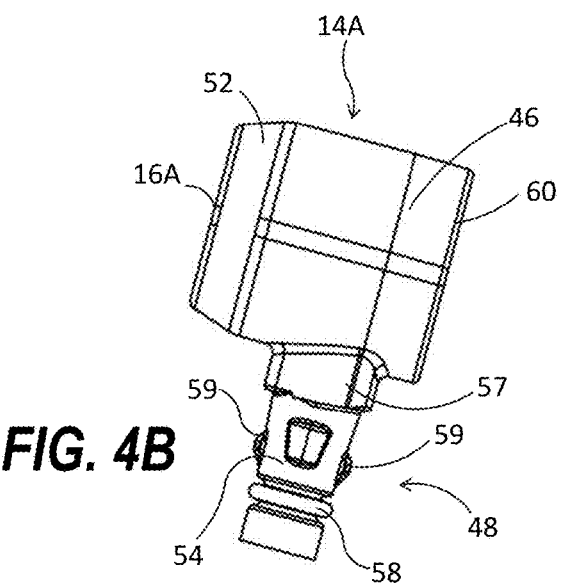
FIG. 4B is a side view of the exemplary first cleansing head of FIG. 4A.

The mounting portion 48 is configured to connect to the mount 24 of the base body 12. The mounting portion 48 may include, for example, a stem 54 extending away from the collection portion 46. The stem 54 may create a channel 56 for directing the fluid flow from the inlet 16A to the opening 26 of the mount 24. The stem 54 may be connected to the collection portion 46 by an intermediate portion 57. The intermediate portion 57 may include a shape that matches a shape of the opening 26 such that the intermediate portion 57 mates with the mount 24 when connected. For example, in one embodiment, the intermediate portion 57 includes a triangular shape. As shown in FIG. 4A, the intermediate portion 57 may include a curved, concave surface that matches a curved, convex portion of the support surface 28. The stem 54 may include an O-ring 58 or other sealing element configured to engage in the opening 26 in the mount 24 and help retain the first cleansing head 14A to the base body 12 and create a tight seal. The stem 54 may further include one or more protrusions 59. The one or more protrusions 59 may be used to further secure the stem 54 in place in the mount 24 of the base body 12. The one or more protrusions 59 may be separated from each other, or may be embodied as a protrusion extending around a circumference of the stem 54.

Figure 4C:
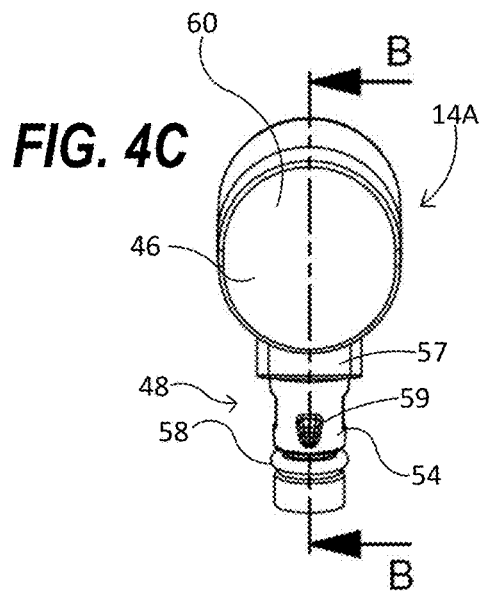
FIG. 4C is a rear view of the exemplary first cleansing head.
Figure 4D:
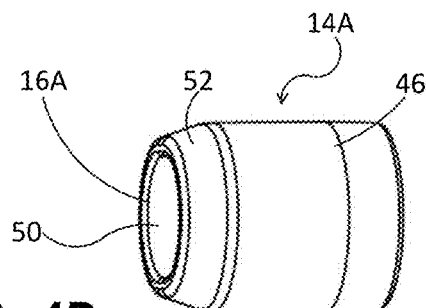
FIG. 4D is a top view of the exemplary first cleansing head.
Figure 4E:
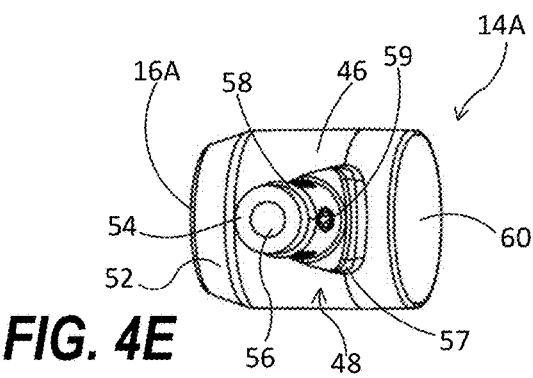
FIG. 4E is a bottom view of the exemplary first cleansing head.
Figure 5A:
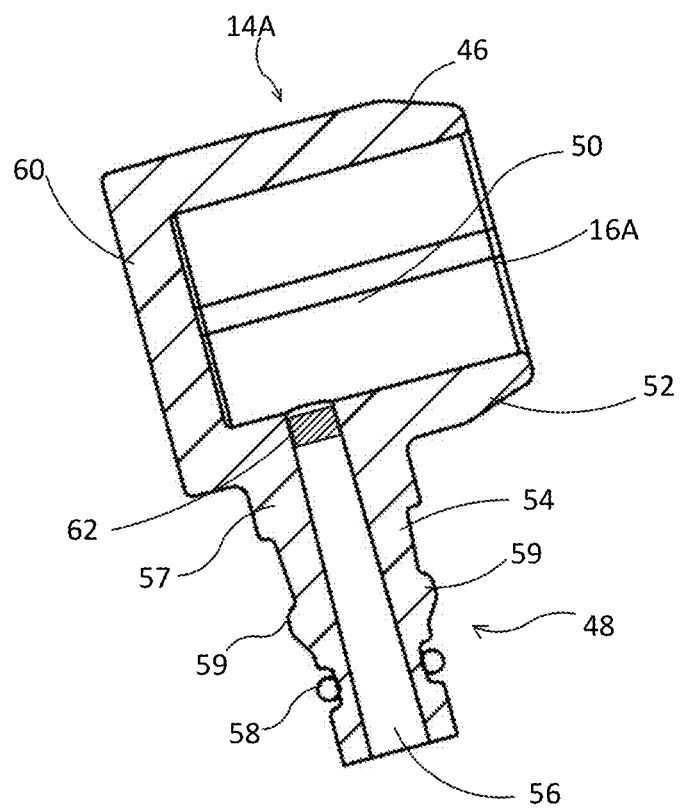
FIG. 5A is a cross-sectional view of the first cleansing head, taken along line B-B of FIG. 4C.

FIG. 5A is a cross-sectional view of the first cleansing head 14A, taken along line B-B of FIG. 4C. This view further illustrates the internal cavity 50 within the collection portion 46. The collection portion 46 may include a back panel 60 that may be removable for ease of cleaning of the first cleansing head 14A. This view also further illustrates the channel 56 of the mounting portion 48 that extends through the stem 54. As shown, the first cleansing head 14A may also include a filter element 62 positioned between the internal cavity 50 and the channel 56. The filter element 62 allows air to flow through but blocks materials that are pulled through the inlet 16A from entering the channel 56. In some embodiments, the filter element 62 may be a valve, such as a one-way valve. In certain embodiments, the first cleansing head 14A is disposable. The first cleansing head 14A collects the unwanted material (e.g., dirt, debris, cleanser, makeup, cosmetics, etc.) in the collection portion 46 preventing the contamination of the base body 12 and its internal components, accordingly additional cleaning or sanitizing of the base body 12 is not required.

FIG. 5B is a cross-sectional view of the cleansing head 14A connected to the base body 12 through the mount 24, taken as a zoomed-in view at the dotted circle of FIG. 3. The stem 54 is inserted into the opening 26 of the mount 24, thereby fluidly connecting the channel 40 with the channel 56. In some embodiments, the stem 54 may generally converge toward the bottom end and generally match a converging shape of the channel 40 in order to allow the stem 54 to easily move within the channel 40 until an interference point is reached. The O-ring 58 may eventually contact the side of the channel 40, thereby restricting movement of the stem 54. The mount 24 may further include a spring clip 63 or other biasing element configured to mate with the one or more protrusions 59 to further retain the cleansing head 14A in the mount 24. The spring clip 63 may be biased inside of the channel 40 but retract as a result of contact with the protrusions 59 as they move further into the channel 40. The spring clip 63 may return to its biased position after the protrusions 59 pass in the channel 40, thereby locking the stem 54 in the channel 40. The connection may be secure but may be removable upon a pulling force. In other embodiments, a spring clip release button may be included.

The support surface 28 includes an inner portion inside of the opening 26 that mates with and/or supports the intermediate portion 57. The collection portion 46 may rest on an outermost part of the support surface 28. Accordingly, the shape of the stem 54, the shape of the channel 40, the O-ring 58, the protrusions 59, the spring clip 63, the support surface 28, the intermediate portion 57, and the collection portion 46 may each contribute to the connection between the cleansing head 14A and the mount 24 of the base body 12, thereby creating a sealed, removable connection that enables a fluid flow from the vacuum pump 30 to the internal cavity 50. However, it should be understood that embodiments are not limited to including each of these connection features, and that alternative embodiments may include one or more of these features to create the connection between the cleansing head 14A and the mount 24. For example, the stem 54 may include one or more indented portions that mate with a second O-ring inside of the channel 40.

FIGS. 6A-6E further illustrate an exemplary embodiment of a second cleansing head 14B. The second cleansing head 14B may be formed as a targeted pore cleansing head that includes an inlet 16B that is smaller than the inlet 16A of the first cleansing head 14A. The second cleansing head 14B, may be, for example, a blackhead cleansing head configured for specific targeting of a blackhead or other type of clogged pore or dirty pore that can be cleaned through the suction force generated by the skin cleansing device 10. The second cleansing head 14B may include similar features to those described above with respect to the first cleansing head 14A, as will be described below. For example, the second cleansing head 14B may also include a collection portion 64 and a mounting portion 66. The second cleansing head 14B may be interchangeably connected to the base body 12 in a same or similar manner as the first cleansing head 14A and features and functions described with respect to the first cleansing head 14A may apply equally to the second cleansing head 14B in at least some embodiments. In certain embodiments, the second cleansing head 14B is disposable. The second cleansing head 14B collects the unwanted material (e.g., dirt, debris, cleanser, blackhead, sebum, etc.) in the collection portion 64 preventing the contamination of the base body 12 and its internal components, accordingly additional cleaning or sanitizing of the base body 12 is not required.

The collection portion 64 may include an internal cavity 68 connected to the inlet 16A. The internal cavity 68 may be formed as a narrow tube. The collection portion 64 may further include an outer housing 70 and an inner nozzle 72. The outer housing 70 may be relatively-movable (e.g., slidable) with respect to the inner nozzle 72. The inner nozzle 72 may form the internal cavity 68 and the inlet 16B. The outer housing 70 may form a shell around the inner nozzle 72 within which the inner nozzle 72 may move. The outer housing 70 may be formed as a rounded, tubular structure with an aperture 74 that is adjacent to and surrounds the inlet 16A. The shape of the outer housing 70 may mate with the shape of the mount 24 of the base body 12 (e.g., the convex shape of a lower portion of the outer housing 70 may match the concave portion of the support surface 28).

Figure 6A:
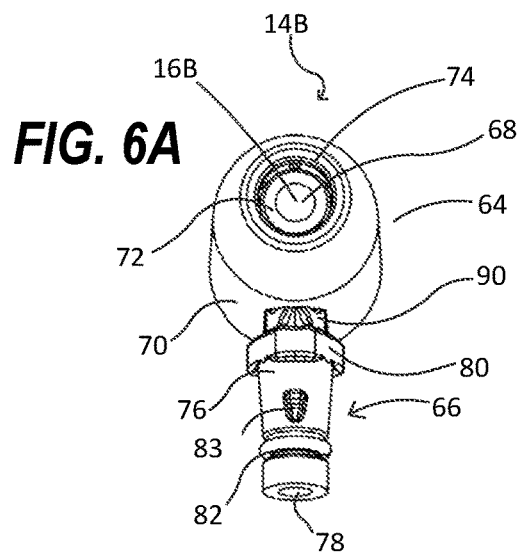
FIG. 6A is a front view of an example embodiment of a second cleansing head.
Figure 6B:
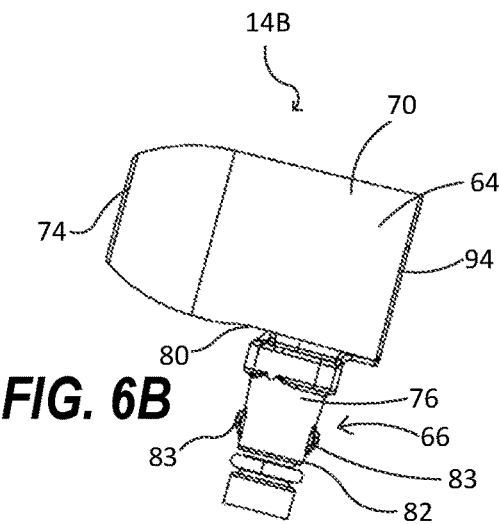
FIG. 6B is a side view of the exemplary second cleansing head of FIG. 6A.

The mounting portion 66 is configured to connect to the mount 24 of the base body 12. The mounting portion 66 may include, for example, a stem 76 extending away from the collection portion 64. The stem 76 may create a channel 78 for directing the fluid flow from the inlet 16B to the opening 26 of the mount 24. The stem 76 may be connected to the collection portion 64 by an intermediate portion 80. The intermediate portion 80 may include a shape that matches a shape of the opening 26 such that the intermediate portion 80 mates with the mount 24 when connected. For example, in one embodiment, the intermediate portion 80 includes a triangular shape. As shown in FIG. 6A, the intermediate portion 80 may include a curved, concave surface that matches a curved, convex portion of the support surface 28. The stem 76 may include an O-ring 82 or other sealing element configured to engage in the opening 26 in the mount 24 and help retain the second cleansing head 14B to the base body 12 and create a tight seal. The stem 76 may also include protrusions 83 that mate with the spring clip 63 in the channel 40 of the base body 12.

Figure 6C:
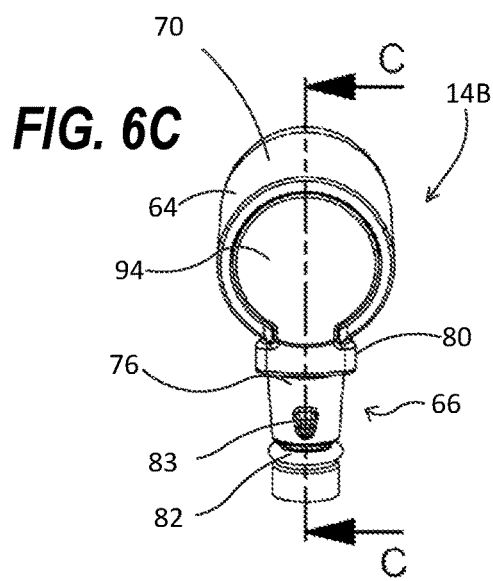
FIG. 6C is a rear view of the exemplary second cleansing head.
Figure 6D:
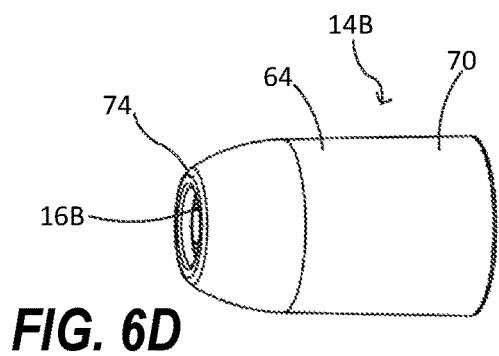
FIG. 6D is a top view of the exemplary second cleansing head.
Figure 6E:
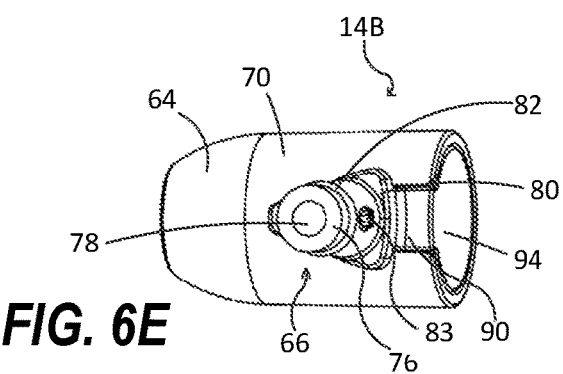
FIG. 6E is a bottom view of the exemplary second cleansing head.

FIG. 7 is a cross-sectional view of the second cleansing head 14B, taken along line C-C of FIG. 6C. This view further illustrates the collection portion 64 and the relative positioning of the inner nozzle 72 inside of the outer housing 70. FIG. 7 further illustrates biasing element 84 that influences the position of the inner nozzle 72 relative to the outer housing 70. For example, the biasing element 84 applies a force to the inner nozzle 72 that maintains the inner nozzle 72 in a retracted position in which the inlet 16A is present in the cavity 68. In an exemplary embodiment, the outer housing 70 includes a bearing surface 86 that contacts a first end of the biasing element 84 and the inner nozzle 72 includes a bearing surface 88 that contacts a second end of the biasing element 84.

The outer housing 70 further includes a slot 90 that receives the stem 76. The slot 90 extends in a direction parallel to a longitudinal direction of the second cleansing head 14B to enable movement of the inner nozzle 72 with respect to the outer housing 70. For example, the slot 90 allows the outer housing 70 to move such that the aperture 74 moves toward the inlet 16A until the inlet 16B is outside of or at least flush with the aperture 74 of the outer housing 70. The movement of the outer housing 70 moves the bearing surface 86 toward the bearing surface 88, compressing the biasing element 84, and exposing the inlet 16B.

FIG. 7 further illustrates that the channel 78 connects to the cavity 68 through an optional filter element 92. In some embodiments, the optional filter element 92 may be a valve, such as a one-way valve. An optional removable back panel 94 may provide access to the filter element 92 and cavity 68 for ease of cleaning. In use, a fluid flow is created from the inlet 16B, through the cavity 68, filter element 92, and channel 78 and into the opening 26 of the base body 12. The vacuum pump 30 generates the fluid flow and the seal between the stem 76 and mount 24 focuses the suction force at the inlet 16B. The outer housing 70 is biased to keep the inlet 16B retracted until a force is applied to move back the outer housing 70 and expose the inlet 16B. This force may be generated, for example, through a user pressing the tip of the outer housing 70 against their skin. This gradual exposure of the inlet 16B to the user's skin helps lead to more comfortable use of the targeted suction force.

FIG. 8A is a side view of the second cleansing head 14B in a first position and FIG. 8B is a side view of the second cleansing head 14B in a second position. In the first position, the second cleansing head 14B includes the inner nozzle 72 retracted into the outer housing 70 through the force of the biasing element 84. In the second position, the outer housing 70 has been moved relative to the inner nozzle 72 such that the inlet 16B is exposed.

FIGS. 9A-9D further illustrate the second cleansing head 14B being connected to the base body 12. As shown, the second cleansing head 14B may be connected to the base body 12 in the same or similar manner as the first cleansing head 14A such that the second cleansing head 14B may be positioned for use. The second cleansing head 14B may extend outwardly from the mount 24. A user may position the inlet 16B adjacent to a target area of the skin for use.

Figure 10A:
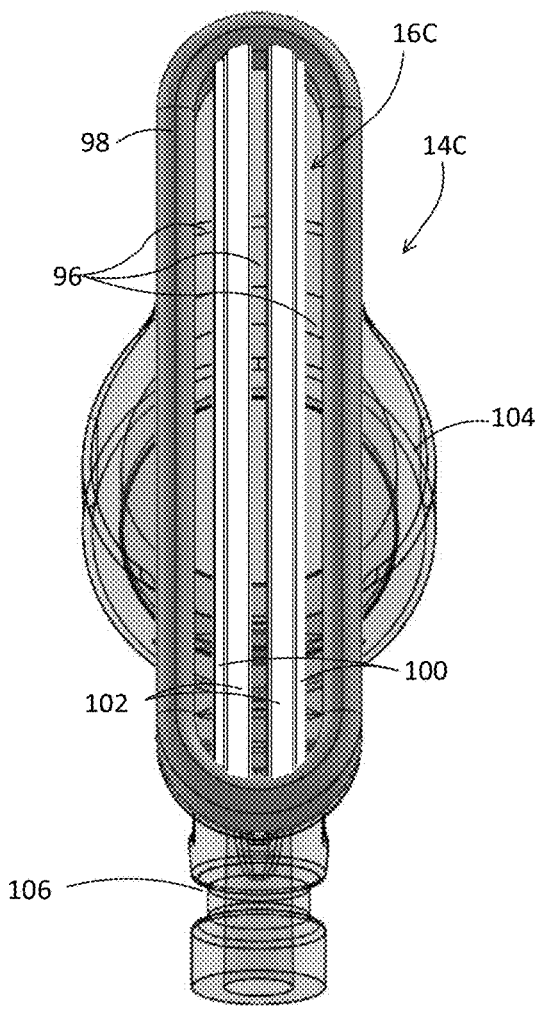
FIG. 10A is a front view of an example embodiment of a third cleansing head.
Figure 10B:
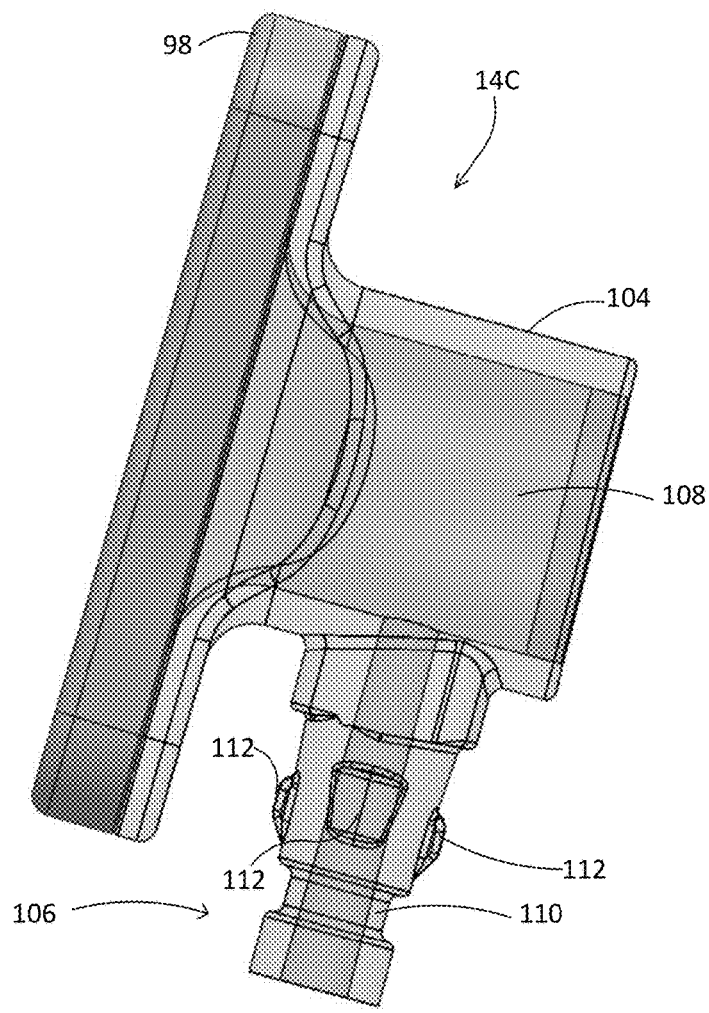
FIG. 10B is a side view of the exemplary third cleansing head of FIG. 10A.

FIGS. 10A-10B illustrate an exemplary embodiment of a third cleansing head 14C. The third cleansing head 14C may be formed as a dermaplaning cleansing head that includes an inlet 16C having one or more air channels 96 that are formed inside of an elongated perimeter wall 98 of the cleansing head 14C. In an exemplary embodiment, the air channels 96 are formed at the sides of one or more dermaplaning blades 100. In some embodiments, one or more abrasive material surfaces 102 are positioned on top of, overlapping with, and/or adjacent to the blades 100.

The third cleansing head 14C may include similar features to those described above with respect to the first cleansing head 14A and/or second cleansing head 14B. For example, the third cleansing head 14C may also include a collection portion 104 and a mounting portion 106. The third cleansing head 14C may be interchangeably connected to the base body 12 in a same or similar manner as the first cleansing head 14A and features and functions described with respect to the first cleansing head 14A may apply equally to the third cleansing head 14C in at least some embodiments. For example, the collection portion 104 may include an internal cavity 108 connected to the inlet 16C for collecting debris. Further, the mounting portion 106 is configured to connect to the mount 24 of the base body 12 via a stem 110 extending away from the collection portion 104. The stem 110 may also include protrusions 112 that mate with the spring clip 63 in the channel 40 of the base body 12. In certain embodiments, the third cleansing head 14C is disposable.

The third cleansing head 14C assists in removing and collects unwanted material (e.g., dirt, debris, cleanser, blackhead, sebum, etc.) in the collection portion 104, thereby preventing the contamination of the base body 12 and its internal components. The blades 100 and abrasive surfaces 102 may assist in removing hair and exfoliation as the third cleansing head 14C passes across the user's skin. The air channels 96 create suction of the skin at the blades 100 and abrasive surfaces 102 and may help to hold the skin at an appropriate angle for dermaplaning and/or exfoliation. The third cleansing head 14C thus provides an additional skin care option for a user of the skin cleansing device 10.

FIGS. 11A-11B illustrate an exemplary embodiment of a fourth cleansing head 14D. The fourth cleansing head 14D may be formed as an abrasive cleansing head that includes an inlet 16D surrounded by an abrasive surface 114. In an exemplary embodiment, abrasive surface 114 includes a plurality of adjacent abrasive sections 116, each with a different level of abrasiveness (e.g., varying degrees of grit, protrusion patterns, abrasive materials, hardness levels, etc.). In an exemplary embodiment, the abrasive surface 114 includes a selected abrasion pattern of the plurality of abrasive sections 116 to enhance skin cleansing and removal of debris and unwanted material from the skin according to a target of each abrasive section 116 (e.g., varying sizes of debris). In an exemplary embodiment, the fourth cleansing head 14D is formed from a plastic (e.g., via molding, laser etching, etc.) and the abrasion pattern is tooled directly into the plastic, thereby not requiring separate attachment of an abrasive material to the head. In some embodiments, the abrasive surface 114 includes a concave configuration leading to the inlet 16D at a center, the inlet 16D of the skin.

The fourth cleansing head 14D may include similar features to those described above with respect to the first cleansing head 14A, second cleansing head 14B, and/or third cleansing head 14C. For example, the fourth cleansing head 14D may also include a collection portion 118 and a mounting portion 120. The fourth cleansing head 14D may be interchangeably connected to the base body 12 in a same or similar manner as the first cleansing head 14A and features and functions described with respect to the first cleansing head 14A may apply equally to the fourth cleansing head 14D in at least some embodiments. For example, the collection portion 118 may include an internal cavity 122 connected to the inlet 16D for collecting debris. Further, the mounting portion 120 is configured to connect to the mount 24 of the base body 12 via a stem 124 extending away from the collection portion 118. The stem 124 may also include protrusions 126 that mate with the spring clip 63 in the channel 40 of the base body 12. In certain embodiments, the fourth cleansing head 14D is disposable.

The skin cleansing device 10 may be used in conjunction with at least one skin care composition, for example, as part of a skin care kit. The skin care composition is preferably an agent that helps maintain, treat, or improve the health or cosmetic appearance of skin. The skin care composition may also help to prepare the skin for a skin cleansing process that uses the skin cleansing device 10. For example, the skin care composition may soften the skin, open pores, or otherwise treat the skin to enhance or improve the results or comfort of the suction force applied by the skin cleansing device 10.

In certain embodiments, the skin cleansing device 10 may be used in conjunction with a pore prep composition comprising about 60% to about 85% w/w water, about 0.01% to about 2% w/w Sallic-210 (Salicylic Acid and Polydextrose and Dextrin and Amylopectin and Niacinamide), about 0.01% to about 2% w/w Disodium EDTA, about 0.01% to about 2% w/w Sepimax Zen (Polyacrylate Crosspolymer-6 and tert-Butyl Alcohol), about 2% to about 15% w/w glycerin, about 0.1% to about 10% w/w diglycerin, about 0.1% to about 10% w/w Matcha Tea Water (*Camellia sinensis* Water and Sodium Benzoate and Sodium Salicylate), about 0.1% to about 10% w/w TEFLOSE (Propanediol and Rhamnose and Glucose and Glucuronic Acid), about 0.1% to about 10% w/w RESISTRESS (Propanediol and Water and *Sophora Japonica* Flower Extract), about 0.01% to about 5% w/w Neosolue-Aqulio (Bis-Ethxoydiglycol Cyclohexane 1,4-Dicarboxylate), about 0.01% to about 5% w/w Purac Ultrapure 90 (Lactic Acid and Water), about 0.01% to about 5% w/w arginine, about 0.01% to about 5% w/w TEGO SOLVE 90 (Polyglyceryl-6 Caprylate and Polyglyceryl-4 Caprate and Water), and about 0.01% to about 5% w/w MICROCARE SB (Water and Sodium Benzoate and Potassium Sorbate). In certain embodiments the skin cleansing device 10 may be used in conjunction with a pore prep composition comprising about 80.19% w/w water, about 0.20% w/w Sallic-210 (Salicylic Acid and Polydextrose and Dextrin and Amylopectin and Niacinamide), about 0.20% w/w Disodium EDTA, about 0.70% w/w Sepimax Zen (Polyacrylate Crosspolymer-6 and tert-Butyl Alcohol), about 8.00% w/w glycerin, about 2.00% w/w diglycerin, about 2.00% w/w Matcha Tea Water (*Camellia sinensis* Water and Sodium Benzoate and Sodium Salicylate), about 2.00% w/w TEFLOSE (Propanediol and Rhamnose and Glucose and Glucuronic Acid), about 2.00% w/w RESIS-TRESS (Propanediol and Water and *Sophora Japonica* Flower Extract), about 0.10% w/w Neosolue-Aqulio (Bis-Ethxoydiglycol Cyclohexane 1,4-Dicarboxylate), about 0.55% w/w Purac Ultrapure 90 (Lactic Acid and Water), about 0.56% w/w arginine, about 1.00% w/w TEGO SOLVE 90 (Polyglyceryl-6 Caprylate and Polyglyceryl-4 Caprate and Water), and about 0.50% w/w MICROCARE SB (Water and Sodium Benzoate and Potassium Sorbate).

Exemplary skin care compositions may include any or all of the following: actives, stability enhancers, microcirculation stimulators, skin calming agents, redness reducers, skin penetration enhancers, exfoliant, solubilizer, preservatives, abrasives, antiacne agents, antidandruff agents, antifungal agents, antimicrobial agents, antioxidants, toners, moisturizers, skin conditioners, lubricants, humectants, emollients, skin bleaching or lightening agents, proteins, cleaners, hair conditioners, and the like.

Actives may be ingredients such as salicylic acid that exfoliate and/or help to soften the skin. Active agents may help to prepare the skin for being exposed to the suction force of the skin cleansing device by unclogging pores or rendering the skin softer and more amenable cleansing.

Abrasives may be used to remove unwanted skin such as dead skin cells and calluses. Exemplary abrasives include but are not limited to the following: alumina, aluminum silicate, apricot seed powder, attapulgite, avocado powder, bamboo powder, barley flour, bentonite, calcium carbonate, calcium phosphate, calcium pyrophosphate, calcium sulfate, chalk, chitin, coconut shell powder, colloidal oatmeal, comfrey leaf powder, corn cob meal or powder, corn flour, corn meal, corn starch, diamond powder, diatomaceous earth, dicalcium phosphate, dicalcium phosphate dehydrate, egg shell powder, Fuller's earth, hydrated silica, hydroxyapatite, kaolin, kiwi seed, lauryl acrylate polymers, loess, magnesium potassium fluorosilicate, magnesium trisilicate, microcrystalline cellulose, montmorillonite, Moroccan lava clay, oat bran, oat flour, oatmeal, oyster shell powder, peach pit powder, peanut flour, pecan shell powder, polyethylene, pumice, raspberry seed, rice bran, rye flour, sand, silica, sodium bicarbonate, sodium hydroxypropyl starch phosphate, sodium magnesium fluorosilicate, sodium silicoaluminate, soybean flour, sweet almond meal, talc, tin oxide, tricalcium phosphate, walnut shell powder, wheat bran, wheat flour, wheat powder, wheat starch, wood powder, zirconium silicate, and derivatives and combinations of these.

Antiacne agents may be used to treat blemishes, pimples, blackheads, and whiteheads. Exemplary antiacne agents include but are not limited to salicylic acid, benzoyl peroxide, carbamide peroxide, hydrogen peroxide, antimicrobial agent, or sulfur, and their derivatives and combinations.

Antidandruff agents may be used to treat dandruff, seborrheic dermatitis, or psoriasis. Exemplary antidandruff agents include but are not limited to the following: coal tar, salicylic acid, selenium sulfide, sulfur, zinc pyrithione, and their derivatives and combinations.

Antifungal agents include agents that inhibit the growth and reproduction of fungal cells or decreases the number of fungi present. Exemplary antifungal agents include but are not limited to the following: calcium undecylenate, ketoconazol, povidone-iodine (PVP-iodine), tea tree oil, undecylenic acid, zinc undecylenate, and their derivatives and combinations.

Antimicrobial agents include agents that kill microorganisms or prevent or inhibit microorganism growth and reproduction or agents that help prevent infection in minor cuts, scrapes, and burns. Exemplary antimicrobial agents include but are not limited to the following: lower chain (C1-C4) alcohols, quaternary ammonium compounds such as benzalkonium chloride and benzethonium chloride, clindamycin, methylbenzethonium chloride, hydrogen peroxide, Oligopeptide-10, phenols, tea tree oil, triclosan, povidone-iodine (PVP-Iodine), and their derivatives and combinations.

Antioxidants include agents that are characterized as free radical scavengers and help reverse skin damage caused by free radicals. Exemplary antioxidants include but are not limited to the following: acetyl cysteine, alpha lipoic acid, arbutin, ascorbic acid (vitamin C), ascorbic acid polypeptide, ascorbyl dipalmitate, ascorbyl methylsilanol pectinate, ascorbyl palmitate, ascorbyl stearate, BHA, BHT, t-butyl hydroquinone, caffeic acid, *Camellia sinensis* oil, carotenoids, chitosan ascorbate, chitosan glycolate, chitosan salicylate, chlorogenic acids, CoQ10, cortisen, cysteine, cysteine HCl, decyl mercaptomethylimidazole, diamylhydroquinone, di-t-butylhydroquinone, dicetyl thiodipropionate, dicyclopentadiene/t-butylcresol copolymer, digalloyl trioleate, dilauryl thiodipropionate, dimyristyl thiodipropionate, dioleyl tocopheryl methylsilanol, diosmine, disodium ascorbyl sulfate, disodium rutinyl disulfate, distearyl thiodipropionate, ditridecyl thiodipropionate, dodecyl gallate, *dunaliella salina* extract, erythorbic acid, ethyl ferulate, ferulic acid, hydroquinone, p-hydroxyanisole, hydroxylamine HCl, hydroxylamine sulfate, hydroxytyrosol, isooctyl thioglycolate, isoquercitrin, kojic acid, madecassicoside, magnesium ascorbate, magnesium ascorbyl phosphate, melatonin, methoxy-PEG-7 rutinyl succinate, methylene di-t-butylcresol, methylsilanol ascorbate, nordihydroguaiaretic acid, octyl gallate, phenylthioglycloic acid, phloroglucinol, potassium ascorbyl tocopheryl phosphate, potassium sulfite, propyl gallate, resveratrol, rosmarinic acid, rutin, sirtunis, sodium ascorbate, sodium ascorbyl/cholesteryl phosphate, sodium bisulfite, sodium erythorbate, sodium metabisulfite, sodium sulfite, sodium thioglycolate, sorbityl furfural, tea tree oil, tetrahexyldecyl ascorbate, tetrahydrodiferuloylmethane, thiodiglycol, thiodiglycolamide, thiodiglycolic acid, thioglycolic acid, thiolactic acid, thiosalicylic acid, thiotaurine, tocophereth derivatives, tocopherol (vitamin E), tocophersolan, tocopheryl acetate, tocopheryl linoleate, tocopherol linoleate/oleate, tocopheryl nicotinate, tocopheryl succinate, tocoquinone, o-tolyl biguanide, tri(nonylphenyl)phosphate, ubiquinone, vitamin D, zinc dibutyldithiocarbamate, and their derivatives and combinations.

Toners include agents that create a tightening or tingling sensation on skin. Exemplary toners include but are not limited to the following: alcohol derivatives such as denatured alcohol and SD alcohol, aluminum derivatives such as aluminum acetate, aluminum bromohydrate, aluminum chloride, aluminum chlorohydrex, aluminum citrate, aluminum diacetate, aluminum dichlorohydrate, aluminum dichlorohydrex, aluminum glycinate, aluminum lactate, aluminum phenolsulfonate, aluminum sesquichlorohydrate, aluminum sesquichlorohydrex, and aluminum sulfate, aluminum zirconium derivatives such as aluminum zirconium octachlorohydrex, aluminum zirconium pentachlorohydrate, aluminum zirconium pentachlorohydrex, aluminum zirconium tetrachlorohydrate, aluminum zirconium tetrachlorohydrex, aluminum zirconium trichlorhydrate, and aluminum zirconium trichlorohydrex, ammonium alum, calcium chloride, calcium lactate, dimethyl MEA, gallic acid, lens *esculenta* (lentil) seed extract, potassium alum, sodium alum, sodium aluminum chlorohydroxy lactate, sodium aluminum lactate, tannic acid, tioxolone, tranexamic acid, zinc acetate, zinc chloride, zinc lactate, zinc phenolsulfonate, zinc sulfate, zirconium chlorohydrate, witch hazel, and their derivatives and combinations.

Skin conditioning agents or moisturizers can be classified into different groups such as emollients, humectants, and occlusive agents. Emollients include agents that remain on the upper layers of skin and act as lubricants and improve appearance. Exemplary emollients include but are not limited to the following: lanolin, glycerides, fruit oils, nut oils, vegetable oils, dimethicones, methicone, cyclomethicone, dormin, fatty acids, myristate derivatives like butyl myristate and myristyl myristate, oleate derivates, C1-C4 glycols, fatty acid glycols, glycol esters, glycerine, glycerols, paraffin, rapeseed oil, long chain alcohols, olive oil, jojoba oil, castor oil, and their derivatives and combinations. Humectants include agents that increase the water content of the top layer of skin. Exemplary humectants include but are not limited to the following: allatoin, agarose, arginine, benzyl hyaluronate, chitosan, copper, corn glycerides, gluconolactone, lactic acid, lactobionic acid, lactose, lysine, kombucha, maltitol, maltose, mannitol, propylene glycol, sodium aspartate, fructose, honey, glycerin, hydroxyethyl urea, and their derivatives and combinations. Occlusive agents slow the evaporation of water from skin. Exemplary occlusive agents include but are not limited to the following: petrolatum, shea butter, dimethicones, plant and animal oils such as avocado, canola, cod liver, and corn, mineral oil, olive oil, soybean oil, lanolin, glycerides, beeswax, triglycerides, long chain fatty alcohols, cocoa butter, coconut oil, jojoba oil, propylene glycol and their derivatives and combinations.

In addition to skin conditioning agents that provide a moisturizing benefit, there are other skin conditioning agents that improve the appearance of skin. Exemplary skin conditioning agents include but are not limited to the following: cholesterol, cystine, hyaluronic acid, keratin, egg yolk, glycine, gluconolactone, lactic acid, lactobionic acid, panthenol, retinol, salicylic acid, vegetable oil, proteins, vitamins, bisabolol, ceramide, coenzyme A, lecithin and their derivatives and combinations.

Skin bleaching or lightening agents include agents that lighten pigment in skin. The preferred skin bleaching agent is hydroquinone. Brighteners include but are not limited to azelaic acid, bearberry, deoxyarbuten, *Glycyrrhiza glabra* (Licorice) root extract, kojic acid, peat extract, and their derivatives and combinations.

Proteins include animal, plant, fungi, yeast, and bacteria proteins that have skin health benefits. Exemplary proteins include but are not limited to the following: collagen, keratin, soy protein, wheat protein, bean palmitate, ascorbic acid polypeptide, the amino acids, casein, cholecalciferol polypeptide, rice protein, silk protein, gluten protein, lysine, acetyl glucosamine, actin, actizyme, albumen, conchiorin protein, corn protein, egg protein, elastin, fibronectin, gaddae protein, hemoglobin, hexapeptide-21, lactalalbumin, lupine protein, maple sycamore protein, milk protein, myristoyl pentapeptide-8, myristoyl tetrapeptide-8, oat protein, oligopeptide 10, palmitoyl hexapeptide-14, palmitoyl oligopeptide, palmitoyl tetrapeptide-7, pea protein, potato protein, reticulin, rice bran protein, serum protein, sweet almond protein, tetrapeptide-16, vegetable protein, yeast protein, palmitoyl oligopeptide, pantothenic acid polypeptides, milk solids, sericin, albumen, amylase, amyloglucosidase, arginine, bromelain, catalase, gelatin, zein, crystallins, cytochrome C, deoxyribonuclease, gliadin, glucose oxidase, glycoproteins, lactoferrin, lactoglubulin, lactoperoxidase, lipase, nisin, oxido reductases, papain, pepsin, subtilisin, sutilains, and their combinations and derivatives.

Cleansers include agents that are used for cleaning the skin and hair by solubilizing oil and suspending soils. Cleansers may be foaming or non-foaming Exemplary cleaners are typically a surfactant and can be characterized as nonionic, anionic, or zwitterionic.

Nonionic surfactants are generally characterized by the presence of an organic hydrophobic group and an organic hydrophilic group. The length of the hydrophilic moiety can be readily adjusted to yield a water dispersible or water soluble compound having the desired degree of balance between hydrophilic and hydrophobic properties. Exemplary nonionic surfactants include the following:

Alkylpolysaccharide surfactants that include a hydrophobic group containing from about 6 to about 30 carbon atoms and a polysaccharide, e.g., a polyglycoside, hydrophilic group containing from about 1.3 to about 10 saccharide units. Any reducing saccharide containing 5 or 6 carbon atoms can be used, e.g., glucose, galactose and galactosyl moieties can be substituted for the glucosyl moieties. Exemplary alkylpolysaccharide surfactants include caproyl ethyl glucoside, caprylyl/capryl glucoside, coco-glucoside, deceth-7 glucoside, decyl glucoside, Condensation products of one mole of a saturated or unsaturated, straight or branched chain alcohol having from about 6 to about 24 carbon atoms with from about 3 to about 50 moles of ethylene oxide. The alcohol moiety can consist of mixtures of alcohols in the above delineated carbon range or it can consist of an alcohol having a specific number of carbon atoms within this range.

Condensation products of one mole of saturated or unsaturated, straight or branched chain carboxylic acid having from about 8 to about 18 carbon atoms with from about 6 to about 50 moles of ethylene oxide. The acid can be a mixture of acids in the above defined carbon atoms range or it can be an acid having a specific number of carbon atoms within the range.

Amine oxides are tertiary amine oxides and semi-polar nonionic surfactants corresponding to the general formula:

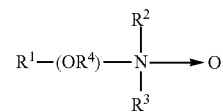

where the arrow=a conventional representation of a semipolar bond; and, $R^1$, $R^2$, and $R^3$ may be aliphatic, aromatic, heterocyclic, alicyclic, or combinations thereof.

Useful amine oxide surfactants are almondamidopropylamine oxide, babassuamidopropylamine oxide, behenamine oxide, cocamidopropyle amine oxide, cocamine oxide, decylamine oxide, decyltetradecylamine oxide, dihydroxyethyl alkoxyalkylamine oxides, dihydroxyalkyl alkylamine oxides, hydrogenated palm kernel amine oxide, hydrogenated tallowamine oxide, alkoxy alkylamine oxides, isostearamidopropylamine oxide, isostearamidopropyl morpholine oxide, lauramidopropylamine oxide, lauramine oxide, methyl morpholine oxide, milkamidopropyl amine oxide, minkamidopropylamine oxide, myrstamidopropylamine oxide, myrstamine oxide, myristyl/cetyl amine oxide, oleamidopropylamine oxide, oleamine oxide, olivamidopropylamine oxide, palmitamidopropylamine oxide, palmitamine oxide, sesamidopropylamine oxide, soyamidopropylamine oxide, stearamidopropylamine oxide, stearamine oxide, tallowamidopropylamine oxide, tallowamine oxide, undecylenamidopropylamine oxide, wheat germamidopropylamine oxide.

Anionic surfactants includes those with a negative charge on the hydrophobic group or surfactants in which the hydrophobic section of the molecule carries no charge unless the pH is elevated to neutrality or above (e.g. carboxylic acids). Carboxylate, sulfonate, sulfate and phosphate are the polar (hydrophilic) solubilizing groups found in anionic surfactants. Cations (counter ions) associated with these polar groups include sodium, lithium, potassium, ammonium, substituted ammonium, calcium, barium, and magnesium.

Anionic surfactants can be subdivided into five major chemical classes: (1) acylamino acids (and salts), such as acylgluamates, acyl peptides, sarcosinates (e.g. N-acyl sarcosinates), taurates (e.g. N-acyl taurates and fatty acid amides of methyl tauride), and the like; (2) carboxylic acids (and salts), such as alkanoic acids (and alkanoates), ester carboxylic acids (e.g. alkyl succinates), ether carboxylic acids, and the like; (3) phosphoric acid esters and their salts; (4) sulfonic acids (and salts), such as isethionates (e.g. acyl isethionates), alkylaryl sulfonates, alkyl sulfonates, sulfosuccinates (e.g. monoesters and diesters of sulfosuccinate), and the like; and (5) sulfuric acid esters (and salts), such as alkyl ether sulfates, alkyl sulfates, and the like Exemplary anionic surfactants include the following:

Linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside (the nonionic nonsulfated compounds being described herein). Exemplary alkyl sulfates include ammonium alkyl sulfates, ammonium cocomonoglyceride sulfates, ammonium dimethicone copolyol sulfate, ammonium laureth sulfates, ammonium lauryl sulfates, ammonium myristyl sulfates, ammonium palm kernel sulfate, diethylamine laureth sulfate, hydroxyethylbutylamine laureth sulfate, magnesium coco-sulfate, magnesium laureth sulfate, monoethanolamine and triethanolamine salts of coco, laureth, and $C_{10}$-$C_{15}$ alkyl sulfates, potassium lauryl sulfate, sodium $C_{12}$-$C_{20}$ alkyl sulfates, sodium laureth sulfates, sodium lauryl sulfate, sodium myristyl sulfate, sodium oleth sulfate, sodium stearyl sulfate, and sodium tallow sulfate.

Ammonium and substituted ammonium (such as mono-, di- and triethanolamine) and alkali metal (such as sodium, lithium and potassium) salts of the alkyl mononuclear aromatic sulfonates such as the alkyl benzene sulfonates containing from 5 to 18 carbon atoms in the alkyl group in a straight or branched chain, e.g., the salts of alkyl benzene sulfonates, such as ammonium dodecylbenzenesulfonate.

Anionic carboxylate surfactants such as alkyl ethoxy carboxylates, the alkyl polyethoxy polycarboxylate surfactants and the soaps (e.g. alkyl carboxyls). Exemplary carboxylate surfactants include magnesium laureth carboxylate, monoethanolamine laureth carboxylate, sodium laureth carboxylates, sodium pareth carboxylates, sodium cocoamide carboxylates, and sodium trideceth carboxylates.

Olefin sulfonates, such as long chain alkene sulfonates, long chain hydroxyalka sulfonates or mixtures of alkenesulfonates and hydroxyalkane-sulfonates, sulfosuccinates, alkyl sulfates, alkyl poly(ethyleneoxy) ether sulfates and aromatic poly(ethyleneoxy) sulfates. Exemplary sulfonates include DEA-methylmyristate sulfonate, magnesium lauryl hydroxypropyl sulfonate, and the like. Exemplary sulfosuccinates include ammonium lauryl sulfosuccinates, diammonium lauryl sulfosuccinates, dioctyl sodium sulfosuccinate, disodum cetearyl sulfosuccinate, disodium cocamido sulfosuccinates, disodium coco-glucoside sulfosuccinate, disodium dimethicone copolyol sulfosuccinate, disodium hydrogenated cottonseed glyceride sulfosuccinate, disodium isostearyl sulfosuccinate, disodium laureth sulfosuccinates, and the like.

Exemplary sarcosinates include sodium C12-C18 sarcosinates, sodium cocoyl sarcosinate, and the like. Exemplary taurates include sodium salts of cocoyl taurate, lauroyl taurate, myristoyl taurate, palmitoyl taurate, and stearoyl taurate Zwitterionic surfactants generally contain cationic and anionic groups which ionize to a nearly equal degree in the isoelectric region of the molecule and which can develop strong "inner-salt" attraction between positive-negative charge centers.

Zwitterionic surfactants include betaines of the general structure:

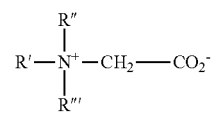

Examples of suitable betaines include almondamidopropyl betaine, apricotamidopropyl betain, avocadamidopropyl betaine, babassuamidopropyl betaine, behenamidopropyl betaine, behenyl betaine, canolamidopropyl betaine, cocamidoethyl betaine, cocamidopropyl betaine, coco-betaine, coco/oleamidopropyl betaine, decyl betaine, lauramidopropyl betaine, myristamidopropyl betaine, myristyl betaine, oleamidopropyl betaine, oleyl betaine, palmamidopropyl betaine, olivamidopropyl betaine, stearyl betaine, and the like.

Preferred cleansers include taurates, sulfates, sulfonates, carboxylates, sulfosuccinates, and sarcosinates, zwitterionic betaines, fatty acid and fatty alcohol derivatives, and alkylpolyglucoside and amine oxide surfactants. In some embodiments, the cleansers may be combined with some abrasives such as clays and sulfurs to provide light exfoliation.

Hair conditioners include agents that enhance the appearance and feel of hair by improving a property like gloss, texture, or body. Exemplary hair conditions include but are not limited to the following: lanolin, silicone, dimethicone, proteins such as amino acids, collagen, and keratin, vitamins, betaine surfactants, amine oxide surfactants, ceramide, fatty acids, eggs, milk, natural plant and animal oils, mineral oil, olive oil, polyquaternium, and their derivatives and combinations.

The skin care agents may be delivered to the skin individually or in a variety of compositions. For example, the skin care agents may be part of a water-thin liquid, thickened liquid, lotion, cream, gel, emulsion or structured liquid, paste, wax, or solid composition. When formulated as a composition, the skin care agents may be present with other skin care agents or additional ingredients that impart a skin care benefit or help in applying the skin care agent. Exemplary additional ingredients include anticaking agents, antifoaming agents, binders, buffers and pH adjusters, dyes, essential oils, and fragrances, chelating agents, corrosion inhibitors, emulsifiers, emulsion stabilizers, film formers, plasticizers, preservatives, propellants, solvents, foaming agents, hydrotropes, UV light absorbers, thickeners, and the like. When the skin care agents are combined with these additional ingredients, they can form exemplary compositions such as shampoos, conditioners, treatments, cleansers, soaps, toners, lotions, moisturizers, masks, serums, gels, scrubs, exfoliants, and wax blocks.

In some embodiments, the skin care agents or skin care compositions are available to users as over-the-counter ("OTC") products, meaning that they are available to users without a doctor's prescription. In some embodiments, the skin care agent or skin care compositions are available to users through a doctor's prescription.

The disclosed embodiments describe a skin cleansing device that includes interchangeable and removable self-enclosed cleansing heads that are connectable to a base body. The skin cleansing device is formed as a hand-held device for personal use and has features and components that create promote ergonomic and comfortable use during a skin cleansing process. The interchangeability of the cleansing heads provides a versatility to the skin cleansing device, thereby enabling differing types of cleaning. The cleansing heads include a blackhead removal cleansing head with movable components for enabling a smooth approach of an inlet toward the user's skin. The skin cleansing device includes aesthetic, ornamental and functional aspects. The skin cleansing device configuration and geometry may have different shapes, arrangements, textures, etc. while achieving the same or equivalent functionality.

Some embodiments of the disclosed system may include a product or kit that includes a base body as a reusable component and a plurality of disposable heads that can be used a limited number of times. This embodiment encourages clean and sanitary use while providing versatility across different types of cleansing heads and enabling multiple users to share the same base body while maintaining use of separate cleansing heads. The disclosed embodiments are applicable to a method of use that includes selecting a cleansing head, installing the cleansing head on the base body, using the device to remove dirt, debris, cosmetic product, etc. from the user's skin, and removing the cleansing head for ease of cleaning and reuse of the base body with the same or a different cleansing head. The removability of the cleansing heads enables easier disposal of the material removed from the skin and helps to provide a long life-cycle of the base body by inhibiting build-up of material and/or clogging of the functional components of the vacuum source. In particular, a composition present on the skin, such as makeup or other topical agents, may be kept separate from the base body such that clogging and build-up is inhibited. Moreover, the disposable cleansing head has a filter and/or sealing element (e.g., gasket, O-ring) such that these elements are changed together with the cleansing head, avoiding build-up and deterioration around these parts. As a result of these combined features, continued use of the base body with an accompanying composition providing a synergistic effect is possible.

Embodiments described herein are directed to a skin care kit. The skin care kit may include a skin care composition as described herein or other commercially available composition. In certain embodiments, the composition is configured to prepare the skin for use with the skin cleansing device disclosed herein. The skin care kit may further include the skin cleansing device, including the base body and at least one removable cleansing head configured to be connected to the base body.

Embodiments described herein are directed to a skin care kit, comprising: a skin care composition; and a skin cleansing device, comprising a base body housing a vacuum pump and comprising a mount, the mount comprising an opening into the base body and a support surface; and at least one removable cleansing head comprising a collection portion and a mounting portion, the collection portion defining an inlet and an internal cavity and the mounting portion comprising a stem defining a channel fluidly connected to the internal cavity, wherein each of the at least one cleansing heads is removably connectable to the base body with the stem being configured to be received in the opening of the mount, and wherein the vacuum pump is configured to generate a fluid flow through the internal cavity and the channel into the base body such that a suction force is generated at the inlet of a cleansing head connected to the base body, wherein the skin care composition is configured to prepare the skin for use with the skin cleansing device.

In certain embodiments, the at least one removable cleansing head of the skin care kit comprises at least a first cleansing head and a second cleansing head. In certain embodiments, the skin care kit contains a first cleansing head and a second cleansing head wherein the inlet of the first cleansing head is larger than the inlet of the second cleansing head. In certain embodiments, the skin care kit comprises a second cleansing head having an outer housing and an inner nozzle, wherein the outer housing is relatively movable with respect to the inner nozzle, and wherein the inner nozzle defines the internal cavity and the inlet.

In certain embodiments, the skin care composition of the skin care kit is a pore prep composition comprising about 60% to about 85% w/w water, about 0.01% to about 2% w/w Sallic-210 (Salicylic Acid and Polydextrose and Dextrin and Amylopectin and Niacinamide), about 0.01% to about 2% w/w Disodium EDTA, about 0.01% to about 2% w/w Sepimax Zen (Polyacrylate Crosspolymer-6 and tert-Butyl Alcohol), about 2% to about 15% w/w glycerin, about 0.1% to about 10% w/w diglycerin, about 0.1% to about 10% w/w Matcha Tea Water (*Camellia sinensis* Water and Sodium Benzoate and Sodium Salicylate), about 0.1% to about 10% w/w TEFLOSE (Propanediol and Rhamnose and Glucose and Glucuronic Acid), about 0.1% to about 10% w/w RESISTRESS (Propanediol and Water and *Sophora*

Japonica Flower Extract), about 0.01% to about 5% w/w Neosolue-Aqulio (Bis-Ethxoydiglycol Cyclohexane 1,4-Dicarboxylate), about 0.01% to about 5% w/w Purac Ultrapure 90 (Lactic Acid and Water), about 0.01% to about 5% w/w arginine, about 0.01% to about 5% w/w TEGO SOLVE 90 (Polyglyceryl-6 Caprylate and Polyglyceryl-4 Caprate and Water), and about 0.01% to about 5% w/w MICROCARE SB (Water and Sodium Benzoate and Potassium Sorbate).

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. The system, components, and processes of the figures are not exclusive. Other systems, components, and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention.

The invention claimed is:

1. A skin care kit, comprising:
   a skin care composition; and
   a skin cleansing device, comprising
      a base body housing a vacuum pump and comprising a mount, the mount comprising an opening into the base body and a support surface; and
      a plurality of disposable cleansing heads comprising a collection portion and a mounting portion, the collection portion defining an inlet and an internal cavity and the mounting portion comprising a stem defining a channel fluidly connected to the internal cavity,
      wherein each of the plurality of disposable cleansing heads is removably connectable to the base body with the stem being configured to be received in the opening of the mount, and
      wherein the vacuum pump is configured to generate a fluid flow through the internal cavity and the channel into the base body such that a suction force is generated at the inlet of a cleansing head connected to the base body,
   wherein the skin care composition is configured to prepare the skin for use with the skin cleansing device.

2. The skin care kit of claim 1, wherein the plurality of disposable cleansing heads comprises at least a first cleansing head and a second cleansing head.

3. The skin care kit of claim 2, wherein the inlet of the first cleansing head is larger than the inlet of the second cleansing head.

4. The skin care kit of claim 3, wherein the second cleansing head comprises an outer housing and an inner nozzle, wherein the outer housing is relatively movable with respect to the inner nozzle, and wherein the inner nozzle defines the internal cavity and the inlet.

5. The skin care kit of claim 1, wherein the skin care composition is a pore prep composition comprising about 60% to about 85% w/w water, about 0.01% to about 2% w/w Sallic-210 (Salicylic Acid and Polydextrose and Dextrin and Amylopectin and Niacinamide), about 0.01% to about 2% w/w Disodium EDTA, about 0.01% to about 2% w/w Sepimax Zen (Polyacrylate Crosspolymer-6 and tert-Butyl Alcohol), about 2% to about 15% w/w glycerin, about 0.1% to about 10% w/w diglycerin, about 0.1% to about 10% w/w Matcha Tea Water (Camellia sinensis Leaf Water and Sodium Benzoate and Sodium Salicylate), about 0.1% to about 10% w/w TEFLOSE (Propanediol and Rhamnose and Glucose and Glucuronic Acid), about 0.1% to about 10% w/w RESISTRESS (Propanediol and Water and Sophora Japonica Flower Extract), about 0.01% to about 5% w/w Neosolue-Aqulio (Bis-Ethxoydiglycol Cyclohexane 1,4-Dicarboxylate), about 0.01% to about 5% w/w Purac Ultrapure 90 (Lactic Acid and Water), about 0.01% to about 5% w/w arginine, about 0.01% to about 5% w/w TEGO SOLVE 90 (Polyglyceryl-6 Caprylate and Polyglyceryl-4 Caprate and Water), and about 0.01% to about 5% w/w MICROCARE SB (Water and Sodium Benzoate and Potassium Sorbate).

6. The skin care kit of claim 1, wherein the disposable cleansing head comprises a filter element positioned between the internal cavity and the channel.

7. The skin care kit of claim 1, wherein the disposable cleansing head comprises at least one protrusion on the stem and the base body comprises a spring clip configured to mate with the at least one protrusion to secure the disposable cleansing head to the base body.

8. The skin care kit of claim 1, further comprising a sealing element positioned on the stem of the disposable cleansing head.

9. The skin care kit of claim 1, further comprising an O-ring positioned on the stem.

10. The skin care kit of claim 1, wherein the disposable cleansing head collects the unwanted material (e.g., dirt, debris, cleanser, blackhead, sebum, etc.) in the collection portion preventing the contamination of the base body and its internal components, wherein additional cleaning or sanitizing of the base body is not required.

11. The skin care kit of claim 1, wherein the plurality of disposable cleansing heads further comprises a third cleansing head formed as a dermaplaning cleansing head, wherein the dermaplaning cleansing head includes an inlet having one or more air channels that are formed inside of an elongated perimeter wall.

12. The skin care kit of claim 11, wherein the one or more air channels are formed at the sides of one or more dermaplaning blades.

13. The skin care kit of claim 12, wherein one or more abrasive material surfaces are positioned on top of, overlapping with, and/or adjacent to the one or more dermaplaning blades.

14. The skin care kit of claim 1, wherein the plurality of disposable cleansing heads further comprises a fourth cleansing head formed as an abrasive cleansing head, wherein the inlet is surrounded by an abrasive surface.

15. The skin care kit of claim 14, wherein the abrasive surface includes a plurality of adjacent abrasive sections, wherein each plurality of adjacent abrasive sections have a different level of abrasiveness selected from varying degrees of grit, protrusion patterns, abrasive materials, hardness levels, or combinations thereof.

16. The skin care kit of claim 14, wherein the abrasive surface includes a plurality of adjacent abrasive sections creating an abrasion pattern of the plurality of abrasive sections to enhance skin cleansing, removal of debris and unwanted material from the skin.

17. The skin care kit of claim 1, wherein the skin care composition is an agent that helps maintain, treat, or improve the health or cosmetic appearance of skin.

18. The skin care kit of claim 1, wherein the skin care composition helps to prepare the skin for a skin cleansing process that uses the skin cleansing device.

19. The skin care kit of claim 1, wherein the skin care composition softens the skin, opens pores, to enhance or improve the results or comfort of the suction force applied by the skin cleansing device.

20. The skin care kit of claim 1, wherein the skin care composition is an exfoliant.

* * * * *